US012704937B2

(12) United States Patent
Roark et al.

(10) Patent No.: US 12,704,937 B2
(45) Date of Patent: Aug. 11, 2026

(54) METHODS, APPARATUSES, AND COMPUTER-READABLE MEDIA FOR ENHANCING DIGITAL PATHOLOGY PLATFORM

(71) Applicant: Gestalt Diagnostics, LLC, Spokane, WA (US)

(72) Inventors: Dan Roark, Spokane, WA (US); Roopam Kakoti, Spokane, WA (US)

(73) Assignee: Gestalt Diagnostics, LLC, Spokane, WA (US)

( * ) Notice: Subject to any disclaimer, the term of this patent is extended or adjusted under 35 U.S.C. 154(b) by 0 days.

(21) Appl. No.: 17/845,670

(22) Filed: Jun. 21, 2022

(65) Prior Publication Data

US 2022/0413682 A1 Dec. 29, 2022

(51) Int. Cl.

| | |
|---|---|
| ***G06F 3/04817*** | (2022.01) |
| ***G06F 3/0482*** | (2013.01) |
| ***G06F 3/04845*** | (2022.01) |
| ***G16H 30/40*** | (2018.01) |

(52) U.S. Cl.

CPC ........ *G06F 3/04817* (2013.01); *G06F 3/0482* (2013.01); *G06F 3/04845* (2013.01); *G16H 30/40* (2018.01)

(58) Field of Classification Search

CPC ............... G06F 3/04817; G06F 3/0482; G06F 3/04845; G06F 3/04842; G16H 30/00; G16H 30/20; G16H 30/40; G16H 10/40

See application file for complete search history.

(56) References Cited

U.S. PATENT DOCUMENTS

| | | | | |
|---|---|---|---|---|
| D427,980 | S | 7/2000 | Hodgson | |
| D428,399 | S | 7/2000 | Kahn et al. | |
| D441,761 | S | 5/2001 | Machida et al. | |
| D468,322 | S | 1/2003 | Walker et al. | |
| D480,401 | S | 10/2003 | Kahn et al. | |
| 6,825,861 | B2 * | 11/2004 | Wasko | G06F 3/0481 715/837 |
| D551,243 | S | 9/2007 | Young | |
| D563,421 | S | 3/2008 | Yamashita et al. | |
| 7,360,167 | B2 * | 4/2008 | Hennum | G06F 3/04842 345/619 |

(Continued)

FOREIGN PATENT DOCUMENTS

| | | |
|---|---|---|
| CN | 305896073 | 7/2020 |
| CN | 306210541 | 12/2020 |

(Continued)

OTHER PUBLICATIONS

The PST Search Report and Written Opinion maiied Dec. 2, 2022 for PCT appiication No. PCT/US22/34360, 15 pages.

(Continued)

*Primary Examiner* — Matthew Ell
*Assistant Examiner* — Blaine T Basom
(74) *Attorney, Agent, or Firm* — Lee & Hayes, P.C.

(57) ABSTRACT

Techniques may include displaying a user interface for a digital pathology platform and displaying a slide panel on the user interface. Displaying the slide panel may include displaying a thumbnail of a digitized image of a specimen, and displaying one or more interactive icons associated with the slide panel. The one or more interactive icons may indicate status associated with the slide panel.

20 Claims, 19 Drawing Sheets

(56) References Cited

U.S. PATENT DOCUMENTS

D576,172 S 9/2008 Kim
D602,036 S 10/2009 Kasuya et al.
D614,192 S 4/2010 Takano et al.
D629,418 S 12/2010 Brown et al.
D635,149 S 3/2011 Viggers et al.
D635,150 S 3/2011 Sykes et al.
D656,152 S 3/2012 Thai et al.
D660,860 S 5/2012 Louch et al.
D665,398 S 8/2012 Carpenter et al.
D679,284 S 4/2013 Rounding et al.
D684,591 S 6/2013 Refuah et al.
D685,810 S 7/2013 Way, Sr. et al.
D689,086 S 9/2013 Philopoulos
D691,619 S 10/2013 Satterfield et al.
D691,620 S 10/2013 Coffman et al.
8,627,222 B2 * 1/2014 Hartwell ................. G06F 16/33 707/765
D708,632 S 7/2014 Baumann
8,996,570 B2 * 3/2015 Stratman ................ G06Q 10/06 382/128
D726,749 S 4/2015 Herried
D738,908 S 9/2015 Herold et al.
D739,412 S 9/2015 Shin et al.
D739,413 S 9/2015 Shin et al.
D751,100 S 3/2016 Lindén et al.
9,292,879 B1 * 3/2016 Lu .......................... G06Q 50/01
D753,715 S 4/2016 Clement et al.
D755,841 S 5/2016 Clement et al.
9,420,945 B2 8/2016 Coelho et al.
9,495,069 B2 * 11/2016 Escobedo ............. G06F 3/0482
D773,486 S 12/2016 Sakuma
D774,052 S 12/2016 Gedrich et al.
9,760,759 B2 * 9/2017 Kyusojin ............... G06V 20/69
D815,133 S 4/2018 Fischer
10,169,680 B1 1/2019 Sachdeva et al.
D843,390 S 3/2019 Protzman et al.
D855,065 S 7/2019 Brown et al.
D858,559 S 9/2019 Kim et al.
D858,564 S 9/2019 Schlereth et al.
D861,012 S 9/2019 Brown et al.
D878,344 S 3/2020 Wu et al.
D880,513 S 4/2020 Wang et al.
D886,142 S 6/2020 Lynne et al.
10,754,638 B1 * 8/2020 Dwivedi ............. G06F 16/9038
10,790,056 B1 9/2020 Accomazzi et al.
D947,208 S 3/2022 Kiikkala et al.
D976,271 S 1/2023 Chen
D976,945 S 1/2023 Christopher
D978,879 S 2/2023 Crone et al.
11,574,140 B2 2/2023 Sue et al.
11,587,654 B2 2/2023 Ginsburg et al.
D981,437 S 3/2023 Lee et al.
11,604,564 B2 3/2023 Vojan et al.
11,615,878 B2 3/2023 Accomazzi et al.
D982,605 S 4/2023 Klahm et al.
11,660,473 B2 5/2023 Vojan et al.
D989,114 S 6/2023 Domm et al.
D990,511 S 6/2023 Chanba et al.
11,705,220 B2 7/2023 Bagaev et al.
D995,555 S 8/2023 Stroier
D997,791 S 9/2023 Wang
D1,001,838 S 10/2023 Lee
D1,003,317 S 10/2023 Silva
D1,009,068 S 12/2023 Rong
D1,027,977 S 5/2024 Kakoti et al.
D1,039,556 S 8/2024 Cichocki et al.
D1,040,846 S 9/2024 Ma et al.
D1,041,492 S 9/2024 Guzmán et al.
D1,042,523 S 9/2024 Chaudhri et al.
D1,043,717 S 9/2024 Boyd et al.
D1,044,843 S 10/2024 Hart et al.
D1,051,143 S 11/2024 Lussier et al.
D1,058,588 S 1/2025 Kakoti et al.
D1,062,756 S 2/2025 Wilson
2003/0016782 A1 1/2003 Kaufman et al.
2003/0160831 A1 * 8/2003 Ball .................... G06F 3/04817 715/835
2006/0212455 A1 * 9/2006 Perry ...................... G06F 16/58
2007/0066348 A1 3/2007 Silverbrook et al.
2008/0100612 A1 5/2008 Dastmalchi et al.
2010/0274587 A1 10/2010 Gamboa et al.
2011/0060766 A1 * 3/2011 Ehlke ..................... G16H 30/00 715/810
2012/0147010 A1 6/2012 Schmidt et al.
2014/0189585 A1 7/2014 Brush et al.
2014/0193052 A1 * 7/2014 Yoshihara ............ G06T 7/0012 382/128
2015/0301732 A1 * 10/2015 Henderson ........... G06T 7/0012 715/781
2015/0379209 A1 12/2015 Kusuma et al.
2016/0019352 A1 1/2016 Cohen et al.
2017/0220754 A1 8/2017 Harrah et al.
2017/0235903 A1 8/2017 McLaughlin et al.
2017/0300641 A1 10/2017 Qerim et al.
2018/0253871 A1 * 9/2018 Bredno ................... G06T 7/174
2018/0356958 A1 12/2018 Yamane et al.
2019/0069153 A1 2/2019 Gideon, III
2019/0154780 A1 5/2019 Traverso et al.
2019/0365350 A1 12/2019 Chiang
2020/0030044 A1 1/2020 Wang et al.
2020/0050655 A1 * 2/2020 Tsujimoto ............ G06F 3/0487
2020/0218817 A1 7/2020 Thrower
2020/0249819 A1 8/2020 Berquam et al.
2020/0265932 A1 8/2020 Ginsburg et al.
2021/0073984 A1 * 3/2021 Locke .................... G06N 20/00
2021/0096897 A1 * 4/2021 Youakim ............ G06F 9/45558
2021/0151158 A1 5/2021 Powell
2021/0166379 A1 6/2021 Smith
2022/0337741 A1 10/2022 Paul et al.
2023/0368346 A1 11/2023 Kakoti
2024/0004540 A1 1/2024 Kakoti
2024/0145081 A1 5/2024 Voll et al.

FOREIGN PATENT DOCUMENTS

| | | |
|---|---|---|
| CN | 306402573 | 3/2021 |
| CN | 308014278 | 5/2023 |
| CN | 202230747716 | 11/2023 |
| EP | 008803928-0005 | 1/2022 |
| EP | 008803928-0006 | 1/2022 |
| EP | 008803928-0007 | 1/2022 |
| GB | 6183071 | 12/2021 |
| GB | 6183070 | 1/2022 |

OTHER PUBLICATIONS

Digital Pathology Moves Forward with Two New Digital Imaging Products, retrieved at <<https://www.darkdaily.com/2009/07/31/digital-pathology-moves-forward-with-two-new-digitial-imaging-products-729/>>, 2019, 1 pg.

Glencoe Software, retrieved Jan. 7, 2023, at <<https://www.glencoesoftware.com/solutions/digital-pathology/>>, 2021, 1 pg.

Office Action for U.S. Appl. No. 29/796,973, mailed on May 5, 2023, Roopam Kakoti, "Display Screen or Portion Thereof Having a Graphical User Interface", 9 pages.

Paige Receives FDA Clearance for the FullFocus Viewer for Digital Pathology, Retrieved Jan. 17, 2023 at <<https://pathologynews.com/industry-news/paige-receives-fda-clearance-for-the-fullfocus-viewer-for-digital-pathology/>>, 2020, 4 pgs.

Proscia, "What is Digital Pathology?", retrieved Jan. 17, 2023 at <<https://proscia.com/company/what-is-digital-pathology/>>, 2020, 1 pg.

Scan-Aperio Digitial Pathology Slide Scanners, retrieved Jan. 17, 2023 at <<https://.leicabiosystems.com/digital-pathology/scan/>>, 2020, 1 pg.

Office Action for U.S. Appl. No. 29/796,973, mailed on Sep. 19, 2023, Kakoti, "Display Screen or Portion thereof Having a Graphical User Interface", 8 pages.

Gestalt PathFlow, "A software platform specifically designed to bring the benefits of digital pathology to pathologists and pathology

(56) References Cited

OTHER PUBLICATIONS laboratories"Publication Date 2024, retrieved Nov. 6, 2024, at <<https://www.gestaltdiagnostics.com/pathflow>>, 3 pages.

Pathologynews, "Paige Launches AI Software to Enable Accurate and Efficient Detection of Breast Cancer Metastases in Lymph Nodes", retrieved Nov. 6, 2024, at <<https://www.pathologynews.com/computational-pathology-ai/paige-launches-ai-software-to-enable-accurate-and-efficient-detection-of-breast-cancer-metastases-in-lymph-nodes/>>, 2022, 1 pg.

Surgicalsciences, "The Articulate Pro study: AI's role in pathology", retrieved Nov. 6, 2024, at <<https://www.youtube.com/watch?v=4BRb09ezULQ&t=39s>>, 2024, 1 pg.

Berg, "G Health Solution platform", retrieved Feb. 26, 2026, at <<http://www.berg.ba/en/g-health-solution/>>, 2026, 2 pages.

ITN, "Paige Unveils Game-Changing AI That Revolutionizes Cancer Detection Across Multiple Tissue Types (/content/paige-unveils-game-changing-ai-revolutionizes-cancer-detectionacross-multi pie-tissue-types)", retrieved Feb. 26, 2026, at <<https://www.itnonline.com/content/paige-unveils-game-changing-ai-revolutionizes-cancer-detection-across-multiple-tissue-types>>, 2024, 1 page.

Indica Labs, "HALO AP 2.0 Features and Functionalities", retrieved Feb. 26, 2025, at <<https://web. archive.org/web/20230322010309/https://indicalab.com/news/halo-ap-2-0-featu res-and-functionalities/>>, 2023, 2 pages. : 2023).

Office Action for U.S. Appl. No. 29/286,400, dated Mar. 5, 2026, 8 Pages.

Pathology in Practice, "Gestalt launches Path Flow update", retrieved Feb. 26, 2026, at <<https://www.pathologyinpractice.com/story/49587/gestalt-launches-pathflow-update>>, 2025, 2 pages.

Search Report for European Application No. 22833923.0, Dated Apr. 25, 2025, 11 pages.

* cited by examiner

METHODS, APPARATUSES, AND COMPUTER-READABLE MEDIA FOR ENHANCING DIGITAL PATHOLOGY PLATFORM

CROSS REFERENCE TO RELATED PATENT APPLICATIONS

This application claims priority to U.S. provisional Patent Application No. 63/215,887, filed on Jun. 28, 2021, entitled "METHODS, APPARATUSES, AND COMPUTER-READABLE MEDIA FOR ENHANCING DIGITAL PATHOLOGY PLATFORM," which is hereby incorporated by reference in its entirety.

BACKGROUND

In pathology, the slide along with the microscope are important artifacts for disease diagnosis. The slide usually includes a label and a stained section of tissue from the original specimen of the patient. The label in turn may contain a barcode which assigns a unique identifier for the slide, patient identifying information (like name, Medical Record Number (MRN), etc., additional information such as stain, body part/specimen type, etc.).

Digital pathology is a sub-field of pathology that focuses on data management based on information generated from digitized specimen slides. Glass slides are converted into Whole Slide Images (WSI) that can be viewed by pathologists on a terminal device without being physically transported. Digital pathology platform is a dynamic, image-based environment that enables the pathologist to review, manage, and analyze pathology information generated from a digitized slide.

While rich data such as annotations may be added to the digitized slide displayed on the digital pathology platform, the information still does not enable the pathologist to know about the existence of such data without looking at the image. Since the pathologist works on a large number of digitized slides on a daily basis, opening the images to check whether such data are presented may slow down the workflow of the pathologist significantly. Therefore, the usability of the digital pathology platform needs to be improved.

BRIEF DESCRIPTION OF THE DRAWINGS

The Detailed Description is set forth with reference to the accompanying figures. The use of the same reference numbers in different figures indicates similar or identical items. The detailed description is set forth with reference to the accompanying figures. In the figures, the left-most digit(s) of a reference number identifies the figure in which the reference number first appears. The use of the same reference numbers in different figures indicates similar or identical items or features. Furthermore, the drawings may be considered as providing an approximate depiction of the relative sizes of the individual applications within individual figures. However, the drawings are not to scale, and the relative sizes of the individual applications, both within individual figures and between the different figures, may vary from what is depicted. In particular, some of the figures may depict applications as a certain size or shape, while other figures may depict the same applications on a larger scale or differently shaped for the sake of clarity.

DETAILED DESCRIPTION

This disclosure is generally directed to digital pathology. More particularly, this disclosure is directed to methods, apparatuses, and computer-readable media for enhancing digital pathology platform.

In various implementations, a user interface for a digital pathology platform may be displayed. A slide panel may be displayed on the user interface. A thumbnail of a digitized image of a specimen may be displayed, and one or more interactive icons associated with the slide panel may be displayed. The one or more interactive icons may indicate status associated with the slide panel.

The techniques described herein may improve the usability of the digital pathology platform.

Figure 1A:
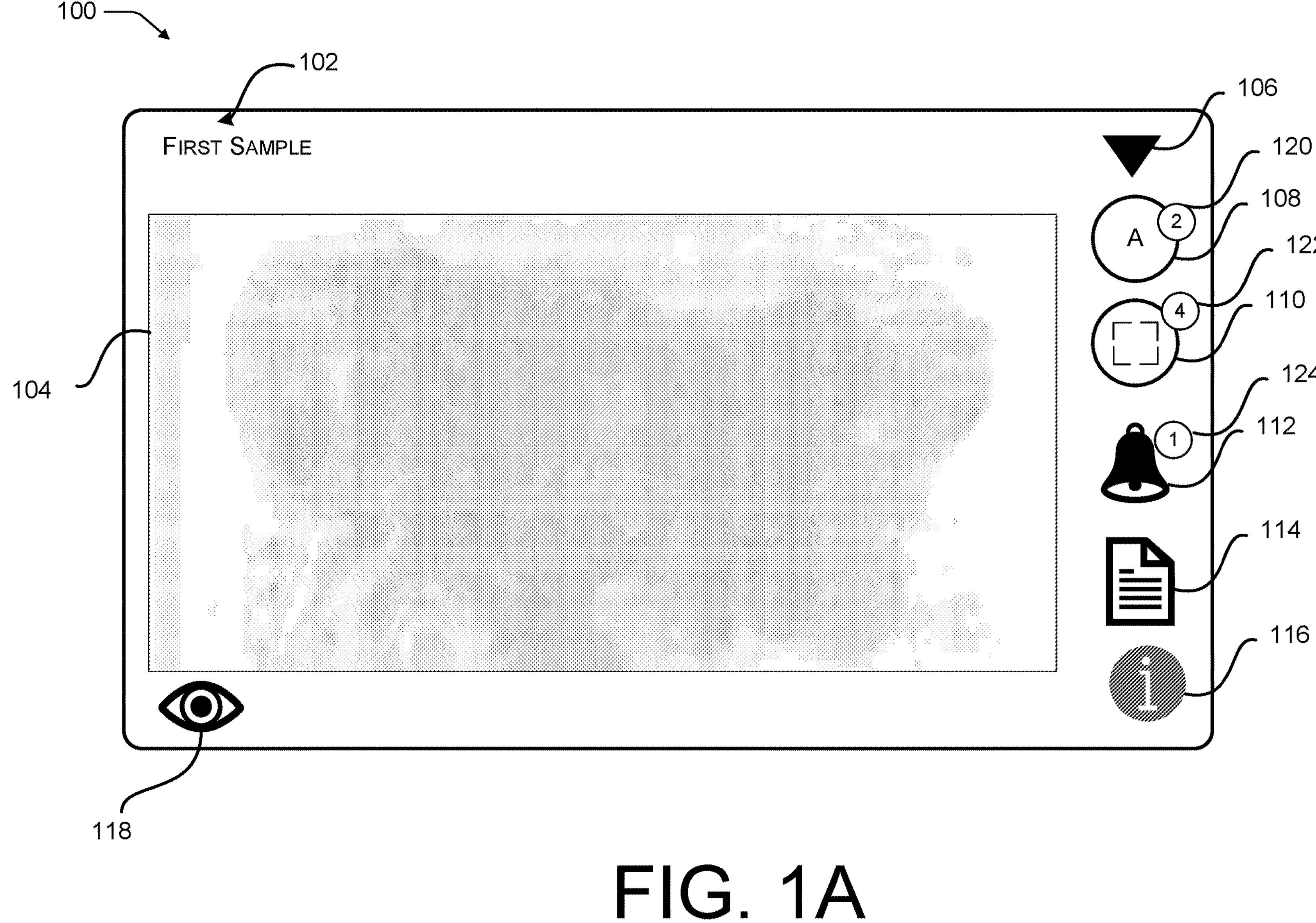
FIG. 1A and FIG. 1B illustrate an example slide panel which may be displayed on a user interface of a digital pathology platform according to implementations of this disclosure.
Figure 1B:
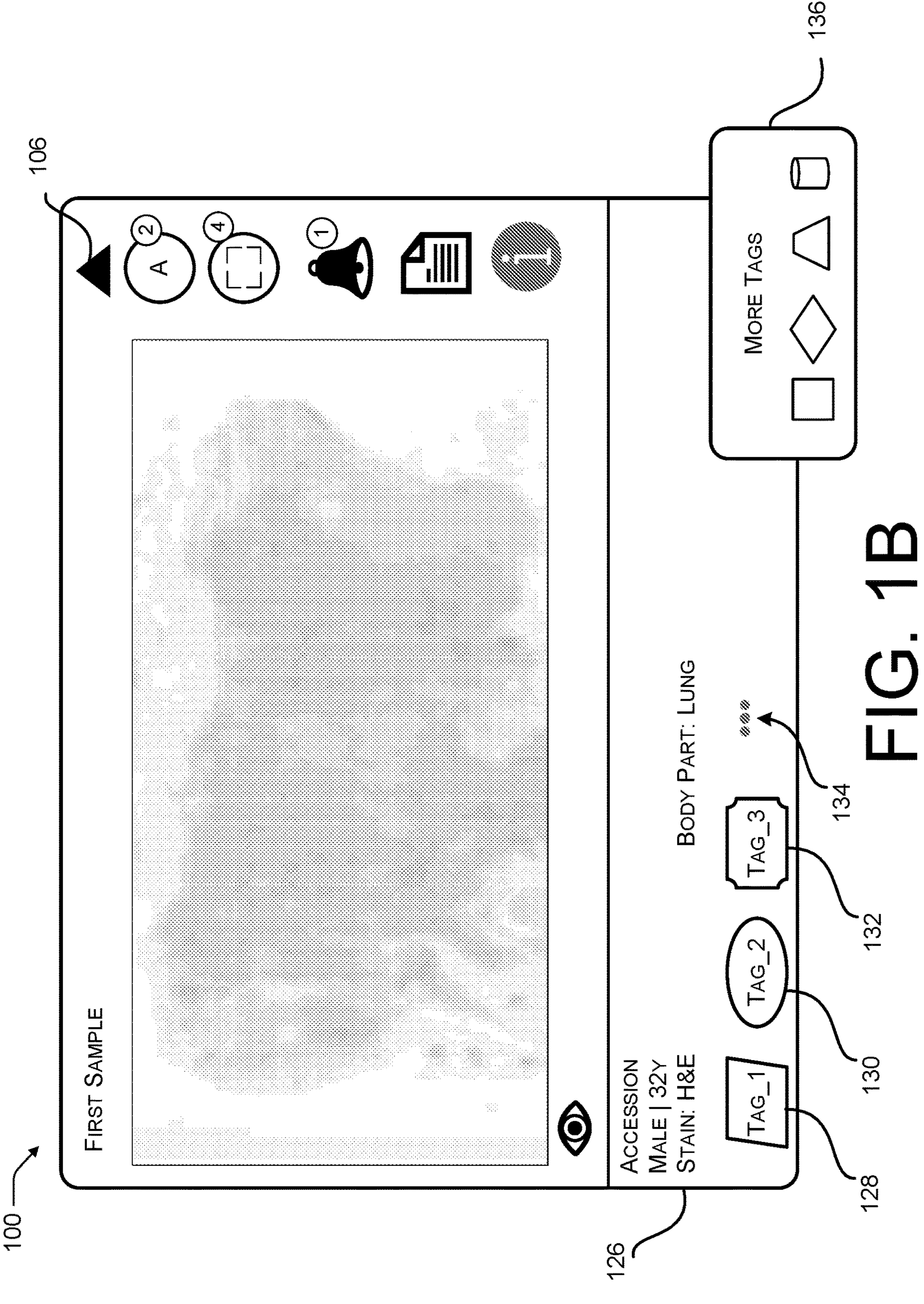

FIG. 1A and FIG. 1B illustrate an example slide panel 100 which may be displayed on a user interface of a digital pathology platform according to implementations of this disclosure.

Referring to FIG. 1A, the slide panel 100 may include an identifier 102, a thumbnail 104 of a digitized image of a specimen, and one or more interactive icons (including but not limited to 106, 108, 110, 112, 114, 116, and 118) associated with the thumbnail 104. The interactive icons are configured to indicate status associated with the slide panel 100. The status associated with the slide panel 100 includes, but is not limited to, whether the slide panel 100 is in a collapsed view mode or an expanded view mode, whether one or more annotations associated with one or more areas of interest of the digitized image of the specimen are available for further operations, whether one or more snapshots of one or more areas of interest of the digitized image of the specimen are available for further operations, whether one or more alerts associated with the digitized image of the specimen are available for further operations, whether a note associated with the digitized image of the specimen is available for further operations, whether additional information associated with the digitized image of the specimen is available for further operations, whether a follow-up action associated with the digitized image of the specimen is required, whether the digitized image of the specimen has been opened, etc.

In implementations, the identifier 102 may be configured to identify the name of the digitized image of the specimen.

In implementations, the thumbnail 104 may be configured to present the digitized image of the specimen in a reduced-size version.

Additionally, the thumbnail 104 may be further configured to be operable. For example, the user may operate the thumbnail 104 by clicking/tapping the thumbnail 104. In response to the operation on the thumbnail 104, the digitized image of the specimen may be displayed.

In implementations, the interactive icons may include a collapse-expand icon 106, an annotation icon 108, a snapshot icon 110, an alert icon 112, a note icon 114, an additional information icon 116, and an action icon 118. Additionally, or alternatively, other icons may be displayed with the slide panel 100. This disclosure is not limited thereto.

In implementations, the collapse-expand icon 106 may be configured to indicate whether the slide panel 100 is in a collapsed view mode or an expanded view mode. For example, the collapse-expand icon 106 may be an inverted triangle, indicating that the slide panel 100 is in the collapsed view mode. For example, the collapse-expand icon 106 may be a triangle, indicating that the slide panel 100 is in the expanded view mode. Though changing the shape of the collapse-expand icon 106 is described here as the manner of indicating whether the slide panel 100 is in a collapsed view mode or an expanded view mode, other manners may be used for the collapse-expand icon 106 to indicate whether the slide panel 100 is in a collapsed view mode or an expanded view mode, such as changing the color of the collapse-expand icon 106, changing the size of the collapse-expand icon 106, and so on. This disclosure is not limited thereto.

Additionally, the collapse-expand icon 106 may be further configured to be operable. For example, the user may operate the collapse-expand icon 106 by clicking/tapping the collapse-expand icon 106. In response to the operation, the slide panel 100 may be switched from the collapsed view mode to the expanded view mode when the slide panel 100 is in the collapsed view mode. Additionally, or alternatively, the slide panel 100 may be switched from the expanded view mode to the collapsed view mode when the slide panel 100 is in the expanded view mode.

In implementations, the annotation icon 108 may be configured to indicate whether one or more annotations associated with one or more areas of interest of the digitized image of the specimen are available for further operations. For example, the annotation icon 108 may be highlighted/unhighlighted to indicate that one or more annotations associated with one or more areas of interest of the digitized image of the specimen are available/unavailable for further operations. Though highlighting/unhighlighting the annotation icon 108 is described here as the manner of indicating that one or more annotations associated with one or more areas of interest of the digitized image of the specimen are available/unavailable for further operations, other manners may be used for the annotation icon 108 to indicate whether one or more annotations associated with one or more areas of interest of the digitized image of the specimen are available for further operations, such as changing the color of the annotation icon 108, changing the size of the annotation icon 108, changing the shape of the annotation icon 108, and so on. This disclosure is not limited thereto.

Additionally, the annotation icon 108 may be further configured to be operable. For example, the user may operate the annotation icon 108 by clicking/tapping the annotation icon 108. In response to the operation on the annotation icon 108, the one or more annotations associated with the one or more areas of interest of the digitized image of the specimen may be displayed. For example, an annotation associated with an area of interest of the digitized image of the specimen may be clinical comments added by a pathologist, such as "tumor", "inflammatory cells", etc.

Additionally, the annotation icon 108 may include an annotation tag 120 which may be configured to indicate a number of the annotations. For example, the annotation tag 120 may show the number "2", indicating that there are two annotations associated with one or more areas of interest of the digitized image of the specimen are available for further operations. In implementations, multiple annotations may be associated with the same area of interest or different areas of interest of the digitized image of the specimen. For example, multiple annotations associated with the same area of interest may be added by different pathologists. For example, multiple annotations associated with the same area of interest may be added at different times. This disclosure is not limited thereto.

In implementations, the snapshot icon 110 may be configured to indicate whether one or more snapshots of one or more areas of interest of the digitized image of the specimen are available for further operations. For example, the snapshot icon 110 may be highlighted/unhighlighted to indicate that one or more snapshots associated with one or more areas of interest of the digitized image of the specimen are available/unavailable for further operations. Though highlighting/unhighlighting the snapshot icon 110 is described here as the manner of indicating that one or more snapshots associated with one or more areas of interest of the digitized image of the specimen are available/unavailable for further operations, other manners may be used for the snapshot icon 110 to indicate whether one or more snapshots associated with one or more areas of interest of the digitized image of the specimen are available for further operations such as changing the color of the snapshot icon 110, changing the size of the snapshot icon 110, changing the shape of the snapshot icon 110, and so on. This disclosure is not limited thereto.

Additionally, the snapshot icon 110 may be further configured to be operable. For example, the user may operate the snapshot icon 110 by clicking/tapping the snapshot icon 110. In response to the operation on the snapshot icon 110, the one or more snapshots associated with the one or more areas of interest of the digitized image of the specimen may be displayed.

Additionally, the snapshot icon 110 may include a snapshot tag 122 which may be configured to indicate a number of the snapshots. For example, the snapshot tag 122 may show the number "4", indicating that there are four snapshots associated with one or more areas of interest of the digitized image of the specimen that are available for further operations. Multiple snapshots may be associated with the same area of interest or different areas of interest of the digitized image of the specimen. For example, multiple snapshots may be taken for the same area of interest with different magnifications such as 40×, 100×, and so on. For example, multiple snapshots may be taken for the same area of interest with different definitions. This disclosure is not limited thereto.

In implementations, the alert icon 112 may be configured to indicate whether one or more alerts associated with the digitized image of the specimen are available for further operations. For example, the alert icon 112 may be highlighted/unhighlighted to indicate that one or more alerts associated with the digitized image of the specimen are available/unavailable for further operations. Though highlighting/unhighlighting the alert icon 112 is described here as the manner of indicating that one or more alerts associated with the digitized image of the specimen are available/unavailable for further operations, other manners may be used for the alert icon 112 to indicate whether one or more alerts associated with the digitized image of the specimen is available for further operations, such as changing the color of the alert icon 112, changing the size of the alert icon 112, changing the shape of the alert icon 112, and so on. This disclosure is not limited thereto.

Additionally, the alert icon 112 may be further configured to be operable. For example, the user may operate the alert icon 112 by clicking/tapping the alert icon 112. In response to the operation on the alert icon 112, the one or more alerts associated with the digitized image of the specimen may be displayed. Additionally, the user may manage the one or more alerts. For example, the user may subscribe to an alert which notifies that the first sample is reviewed by a certain pathologist. In that case, when the first sample is reviewed by the certain pathologist, the alert icon 112 associated with the first sample may be highlighted, indicating that an alert is available for further operation. The user may click the alert icon 112, and the content of the alert may be displayed, indicating that the first sample is reviewed by the certain pathologist.

Additionally, the alert icon 112 may include an alert tag 124 which may be configured to indicate a number of the alerts. For example, the alert tag 124 may show the number "1", indicating that there is one alert associated with the digitized image of the specimen that is available for further operations.

In implementations, the note icon 114 may be configured to indicate whether a note associated with the digitized image of the specimen is available for further operations. For example, the note icon 114 may be highlighted/unhighlighted to indicate that a note associated with the digitized image of the specimen is available/unavailable for further operations. Though highlighting/unhighlighting the note icon 114 is described here as the manner of indicating that a note associated with the digitized image of the specimen is available/unavailable for further operations, other manners may be used for the note icon 114 to indicate whether a note associated with the digitized image of the specimen is available for further operations, such as changing the color of the note icon 114, changing the size of the note icon 114, changing the shape of the note icon 114, and so on. This disclosure is not limited thereto.

Additionally, the note icon 114 may be further configured to be operable. For example, the user may operate the note icon 114 by clicking/tapping the note icon 114. In response to the operation on the note icon 114, the note associated with the digitized image of the specimen may be displayed.

In implementations, the additional information icon 116 may be configured to indicate whether additional information associated with the digitized image of the specimen is available for further operations. For example, the additional information icon 116 may be highlighted/unhighlighted to indicate that additional information associated with the digitized image of the specimen is available/unavailable for further operations. Though highlighting/unhighlighting the additional information icon 116 is described here as the manner of indicating that additional information associated with the digitized image of the specimen is available/unavailable for further operations, other manners may be used for the additional information icon 116 to indicate whether additional information associated with the digitized image of the specimen is available for further operations, such as changing the color of the additional information icon 116, changing the size of the additional information icon 116, changing the shape of the additional information icon 116, and so on. This disclosure is not limited thereto.

Additionally, the additional information icon 116 may be further configured to be operable. For example, the user may operate the additional information icon 116 by clicking/tapping the additional information icon 116. In response to the operation on the additional information icon 116, the additional information may be displayed. For example, the additional information may include, but is not limited to, the image type of the digitized image of the specimen (such as Portable Network Graphics (PNG), Joint Photographic Expert Group (JPEG), and so on), the image size and resolution, the brand/model/type of the scanner which scans the specimen to generate the digitized image, the scan magnification, etc.

In implementations, the action icon 118 may be configured to indicate whether a follow-up action associated with the digitized image of the specimen is required. For example, the action icon 118 may be highlighted/unhighlighted to indicate that a follow-up action associated with the digitized image of the specimen is required/unrequired. Though highlighting/unhighlighting the action icon 118 is described here as the manner of indicating that a follow-up action associated with the digitized image of the specimen is required/unrequired, other manners may be used for the action icon 118 to indicate whether a follow-up action associated with the digitized image of the specimen is required, such as changing the color of the action icon 118, changing the size of the action icon 118, changing the shape of the action icon 118, and so on. This disclosure is not limited thereto. In implementations, the follow-up action may include reviewing by another pathologist. For example, the user may require another pathologist to review the first sample.

Additionally, action icon 118 may be further configured to be operable. For example, the user may operate the action icon 118 by clicking/tapping the action icon 118. In response to the operation on the action icon 118, the slide panel 100 may be switched from a normal state to a hidden state when the slide panel 100 is in the normal state. Additionally, or alternatively, in response to the operation on the action icon 118, the slide panel 100 may be switched from the hidden state to the normal state when the slide panel 100 is in the hidden state.

In the normal state, the slide panel 100 may be displayed without additional visual effects. In the hidden state, the slide panel 100 may be displayed without additional visual effects, such as blur, shadow, and so on. This disclosure is not limited thereto. The state change of the slide panel 100 provides convenience for the user. The user may see whether the slide panel 100 requires follow-up action from the appearance of the slide panel 100 directly without opening the digital image to check further data, and the usability of the digital pathology platform is improved.

Referring to FIG. 1B, the collapse-expand icon 106 is in a triangle shape, indicating that the slide panel 100 is in the expanded view mode. The expanded part 126 of the slide panel 100 may be shown in the expanded view mode. For example, the expanded part 126 of the slide panel 100 may show information such as the source of the specimen, the stain type of the specimen, the body part of the specimen, and tags (such as tag_1 128, Tag_2 130, and tag_3 132) associated with the specimen.

In implementation, the tags associated with the specimen may be configured to be an index to indicate more information associated with the specimen. For example, various shapes of the tags may indicate various categorizations of the specimen. Additionally, more information associated with the specimen may be indicated through other manners such as various colors, various greyscales, and so on of the tags. This disclosure is not limited thereto.

In implementations, the expanded part 126 of the slide panel 100 may further include a more tags icon 134. The more tags icon 134 may be configured to be operable. For example, the user may operate the more tags icon 134 by clicking/tapping the more tags icon 134. In response to the operation on the more tags icon 134, a pop-up window 136 may be displayed. The pop-up window 136 may show more tags for the user to select.

With the slide panel 100, the one or more interactive icons enable the user to know the status associated with the slide panel 100 without opening the digitized image of the specimen. Additionally, the one or more interactive icons are operable such that the user may view the data associated with the slide panel such as annotations, snapshots, alerts, notes, additional information, follow-up action requirements, and so on by operating the one or more interactive icons without opening the digitized image of the specimen. The usability of the digital pathology platform may be improved. The workflow of the user may be facilitated.

Figure 2A:
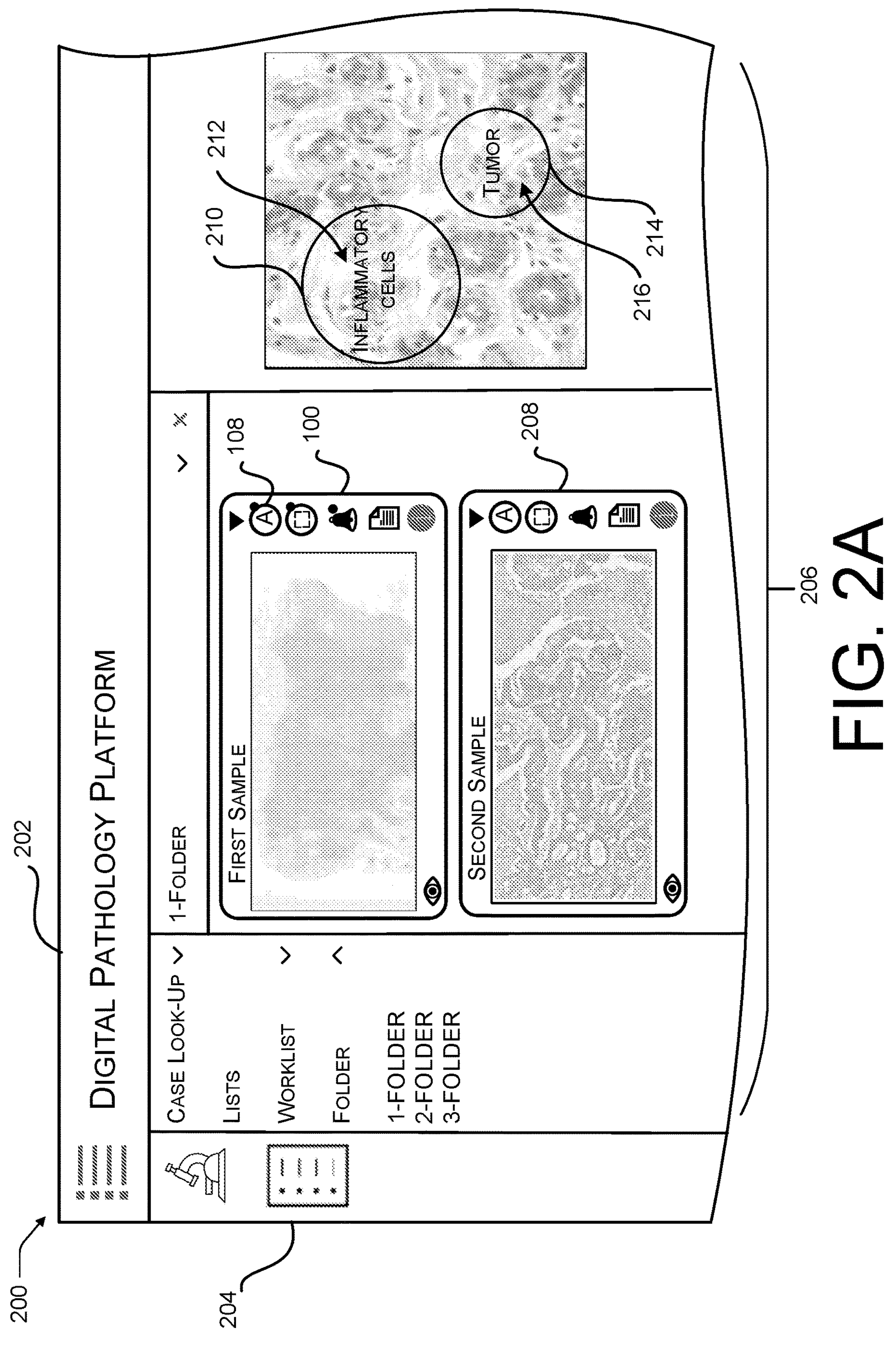
FIG. 2A and FIG. 2B illustrate an example user interface of a digital pathology platform according to implementations of this disclosure.
Figure 2B:
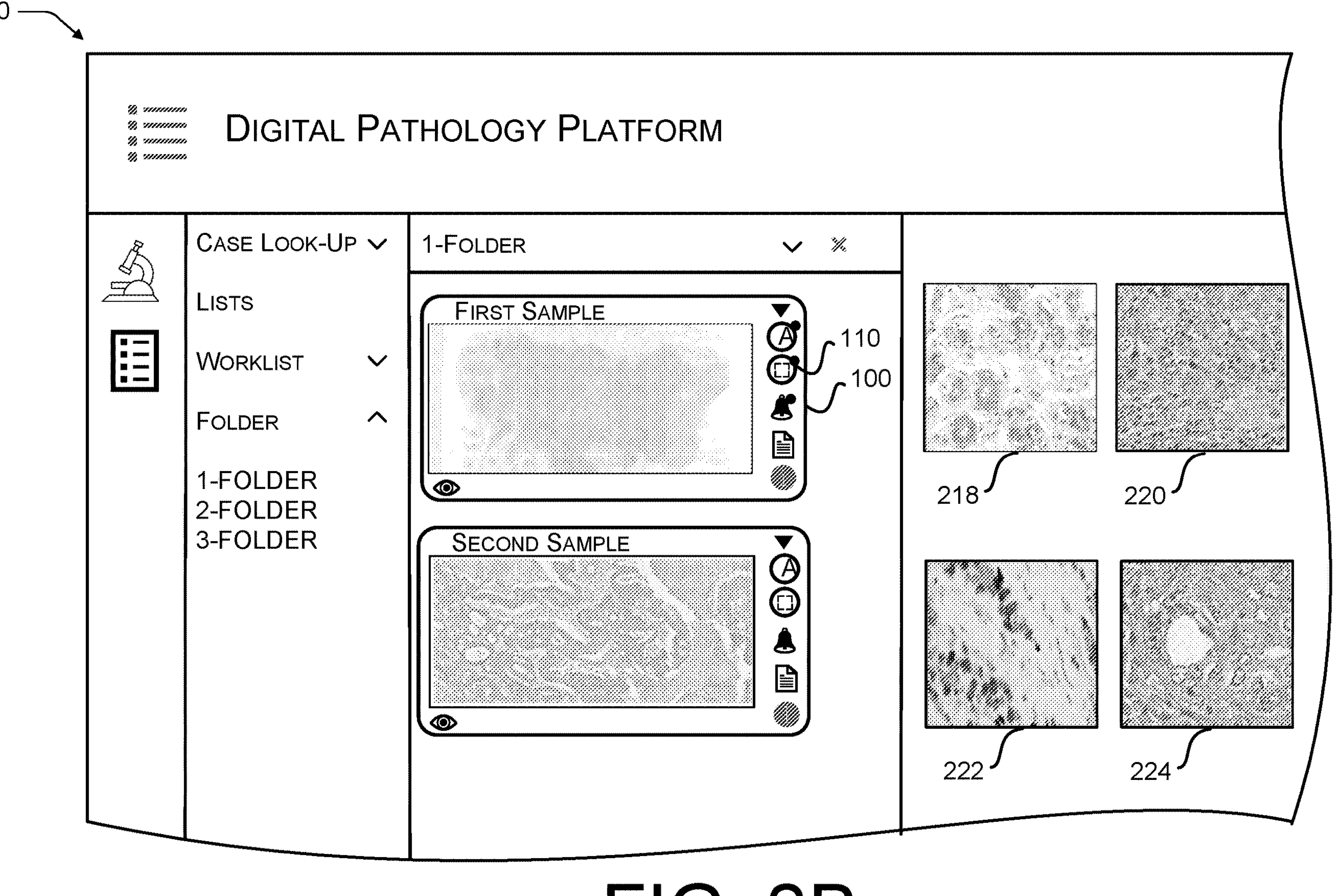

FIG. 2A and FIG. 2B illustrate an example user interface 200 of a digital pathology platform according to implementations of this disclosure.

Referring to FIG. 2A, the user interface 200 may include a header 202, a sidebar 204, and a main display area 206.

In implementations, the header 202 may be configured to show the name of the digital pathology platform.

In implementations, the sidebar 204 may be configured to show buttons of applications (Apps). A button is an interactive element on the user interface 200 that enables the user to directly communicate with the user interface. An application is a type of software that allows the user to perform tasks and may be integrated with the digital pathology platform.

In implementations, the main display area 206 may be configured to display texts, graphics, images, directories, background details, etc. This disclosure is not limited thereto.

For example, the main display area 206 may display slide panel “first sample” 100 and slide panel “second sample” 208.

As an example, the user may operate the annotation icon 108 by clicking/tapping the annotation icon 108. In response to the operation on the annotation icon 108, a first area of interest 210 and a first annotation 212 associated with the first area of interest 210, and a second area of interest 214 and a second annotation 216 associated with the second area of interest 214 may be displayed in the main area 206 of the user interface 200. Other numbers of areas of interest and associated annotations may be shown. Multiple annotations may be associated with the same area of interest. For example, annotations associated with areas of interest of the digitized image of the specimen may be clinical comments added by a pathologist, such as “tumor”, “inflammatory cells”, etc. This disclosure is not limited thereto. Additional details of the annotations are described throughout this disclosure and are not repeated here.

Referring to FIG. 2B, as an example, the user may operate the snapshot icon 110 by clicking/tapping the snapshot icon 110. In response to the operation on the snapshot icon 110, a first snapshot 218, a second snapshot 220, a third snapshot 222, and a fourth snapshot 224 may be displayed in the main area 206 of the user interface 200. Other numbers of snapshots may be shown. Multiple snapshots may be associated with the same area of interest or different areas of interest. For example, multiple snapshots may be taken for the same area of interest with different magnifications such as 40×, 100×, and so on. This disclosure is not limited thereto. Additional details of the snapshots are described throughout this disclosure and are not repeated here.

With the user interface 200, the one or more interactive icons enable the user to view the associated data such as annotations, snapshots, and so on by operating the one or more interactive icons without opening the digitized image of the specimen. The usability of the digital pathology platform may be improved. The workflow of the user may be facilitated.

Figure 3A:
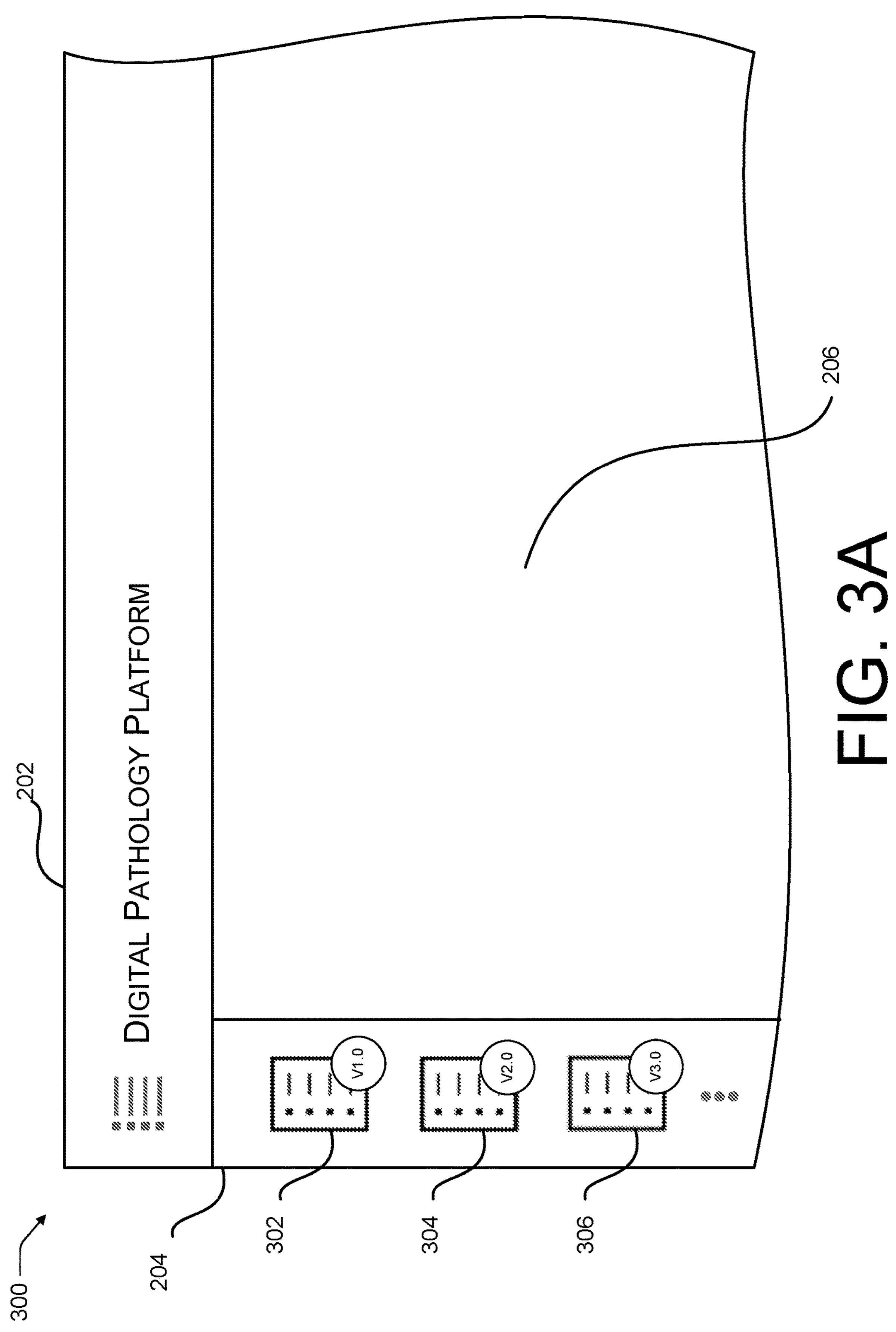
FIG. 3A, FIG. 3B, and FIG. 3C illustrate an example user interface of a digital pathology platform according to implementations of this disclosure.
Figure 3B:
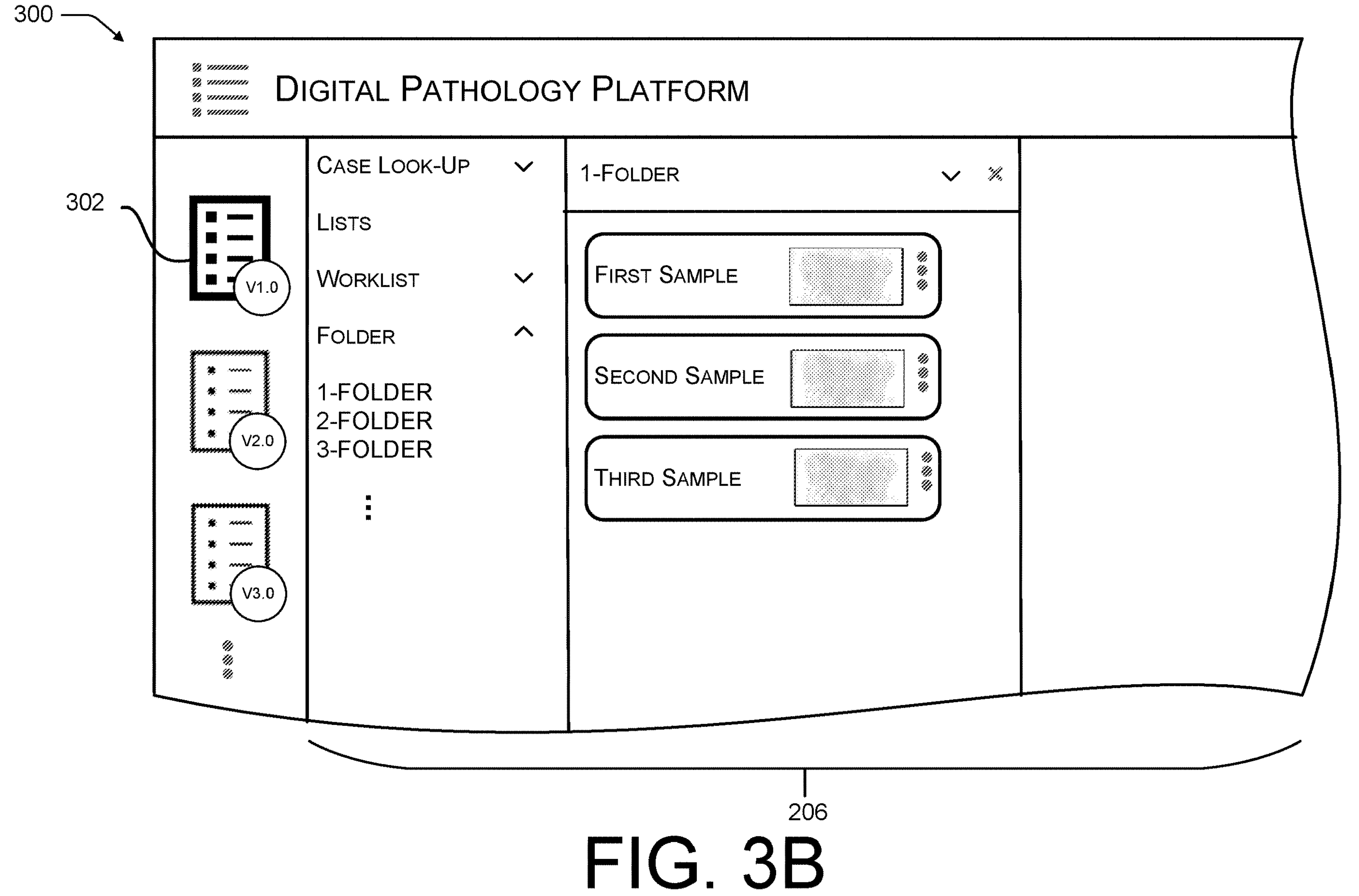
Figure 3C:
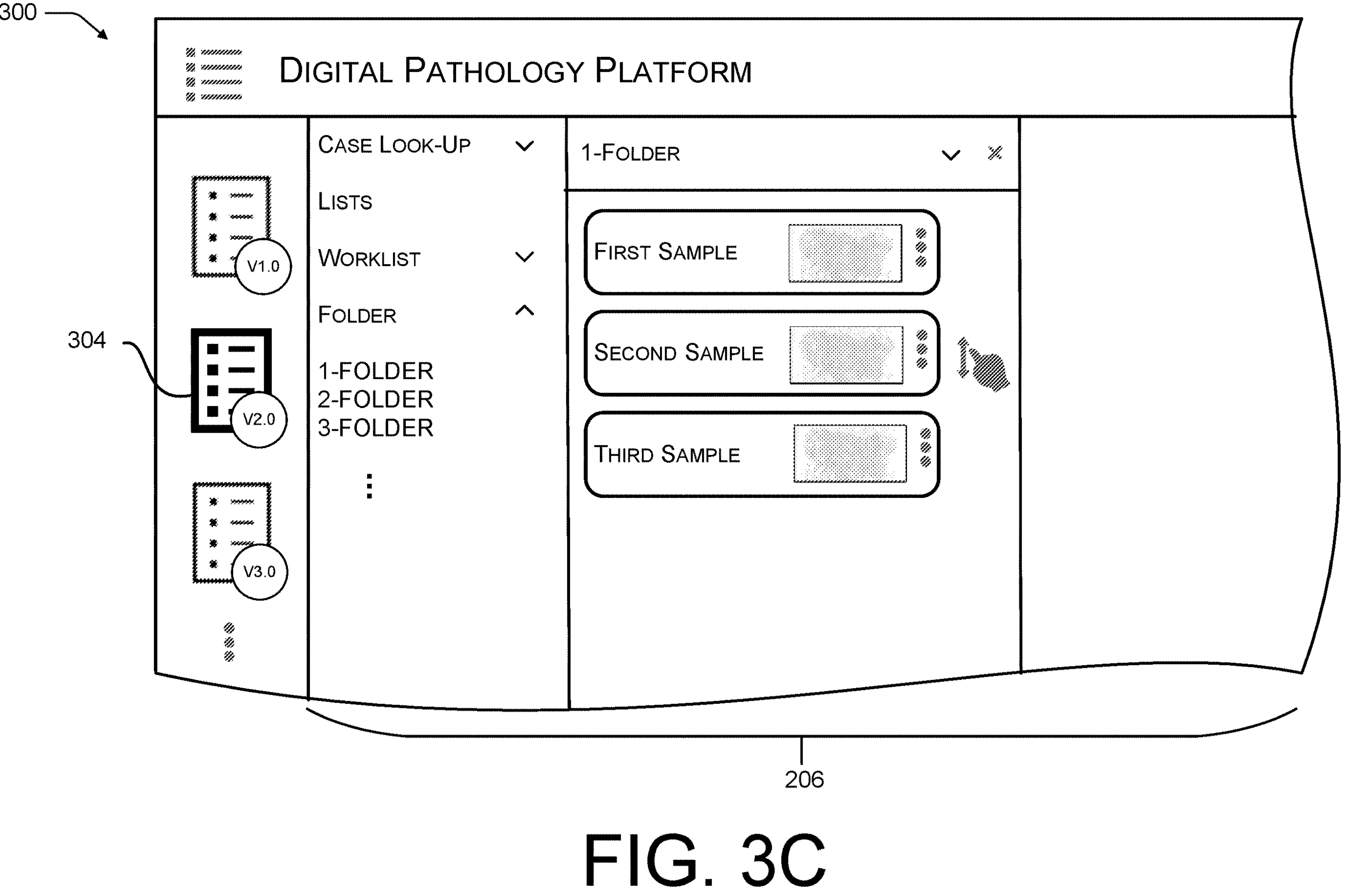

FIG. 3A, FIG. 3B, and FIG. 3C illustrates an example user interface 300 of a digital pathology platform according to implementations of this disclosure.

Referring to FIG. 3A, the user interface 300 may have the same arrangement as the user interface 200. The user interface 300 may include a header 202, a sidebar 204, and a main display area 206.

In implementations, the sidebar 204 may include a first button 302 of a first version of an application, a second button 304 of a second version of the application, a third button 306 of a third version of the application, etc.

Referring to FIG. 3B, the user may operate the first button 302 by clicking/tapping the first button 302. In response to the operation on the first button 302, the first version of the application may be displayed in the main display area 206.

Referring to FIG. 3C, the user may operate the second button 304 by clicking/tapping the second button 304. In response to the operation on the second button 304, the second version of the application may be displayed in the main display area 206.

In implementations, the second version of the application may include improved features that are not available in the first version of the application. For example, with the second version of the application, the user may change the order of slide panels by dragging and dropping the slide panels. On the other hand, the order of slide panels may not be changed in the first version of the application.

With the user interface 300, various versions of the same application may be accessible to the user at the same time. In practice, when a new version of an application is released, the user may need to be trained for several weeks to learn how to use the new version of the application. During the training period, the user may use the old version of the application to work. Additionally, the user may need to use different versions of the application for other reasons. This disclosure is not limited thereto. Thus, the usability of the digital pathology platform is improved. The workflow of the user may be facilitated.

FIG. 4A, FIG. 4B, FIG. 4C, FIG. 4D, FIG. 4E, FIG. 4F, FIG. 4G, FIG. 4H, FIG. 4I, FIG. 4J, and FIG. 4K illustrate an example process 400 for enhancing digital pathology platform according to implementations of this disclosure.

Figure 4A:
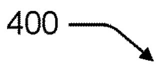
FIG. 4A, FIG. 4B, FIG. 4C, FIG. 4D, FIG. 4E, FIG. 4F, FIG. 4G, FIG. 4H, FIG. 4I, FIG. 4J, and FIG. 4K illustrate an example process for enhancing digital pathology platform according to implementations of this disclosure.
Figure 4A:
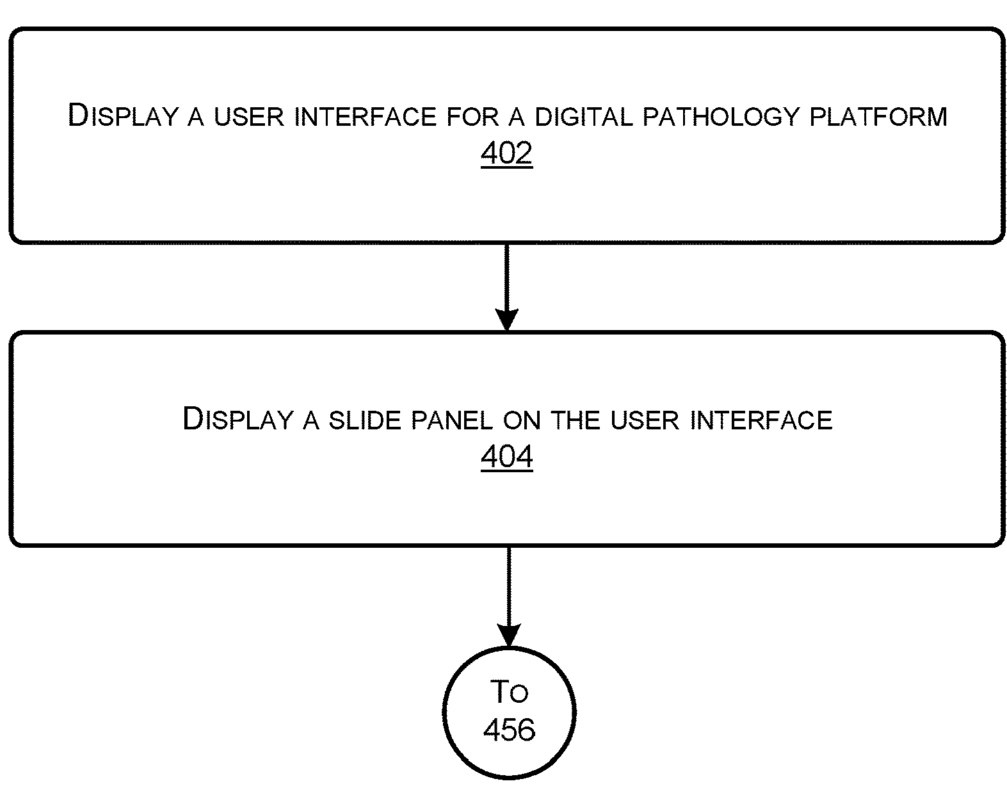

Referring to FIG. 4A, process 400 may include the following.

At block 402, operations may include displaying a user interface for a digital pathology platform.

At block 404, operations may include displaying a slide panel on the user interface. Additional details of the slide panel are described throughout the disclosure and are not repeated here.

Figure 4B:
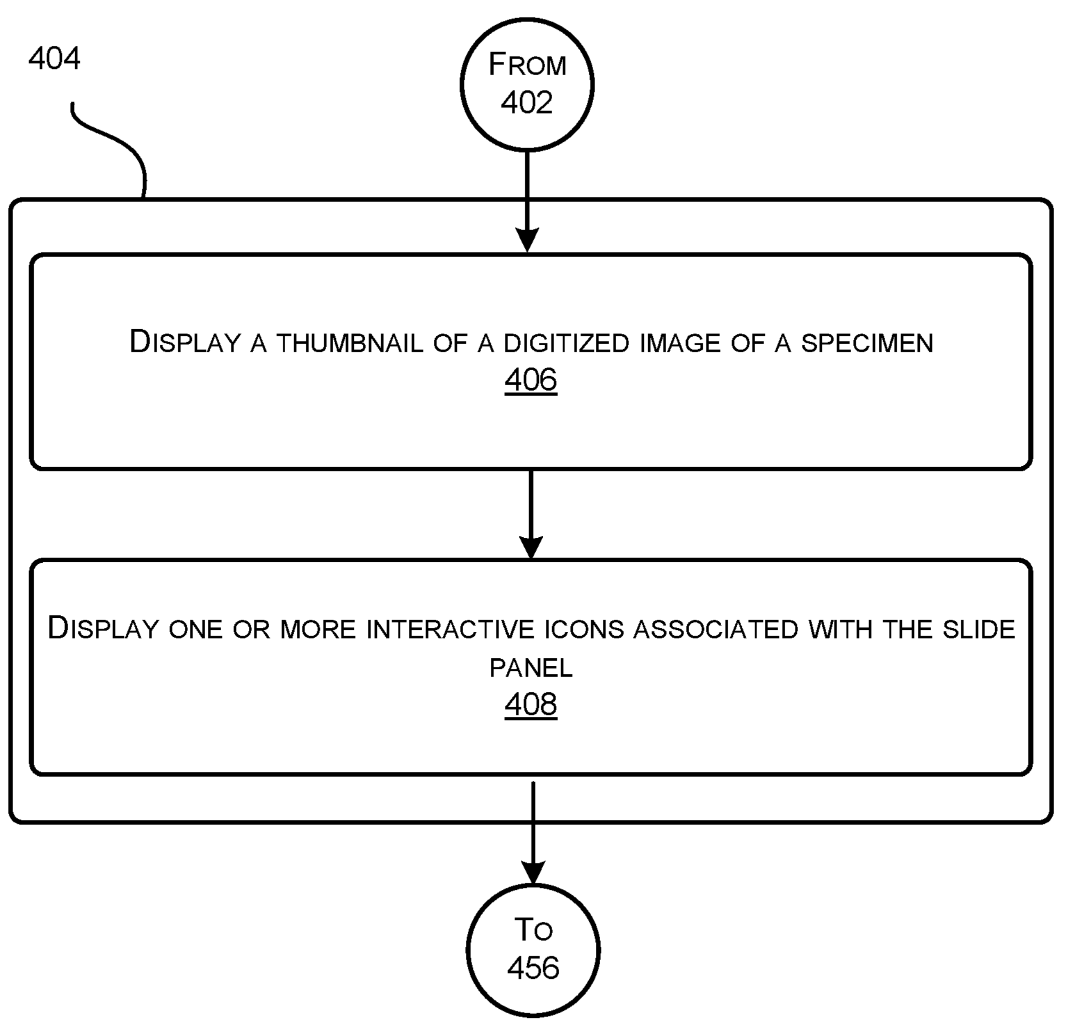

Referring to FIG. 4B, block 404 may include the following.

At block 406, operations may include displaying a thumbnail of a digitized image of a specimen. Additional details of the thumbnail are described throughout the disclosure and are not repeated here.

At block 408, operations may include displaying one or more interactive icons associated with the slide panel. The one or more interactive icons indicating status associated with the slide panel.

Figure 4C:
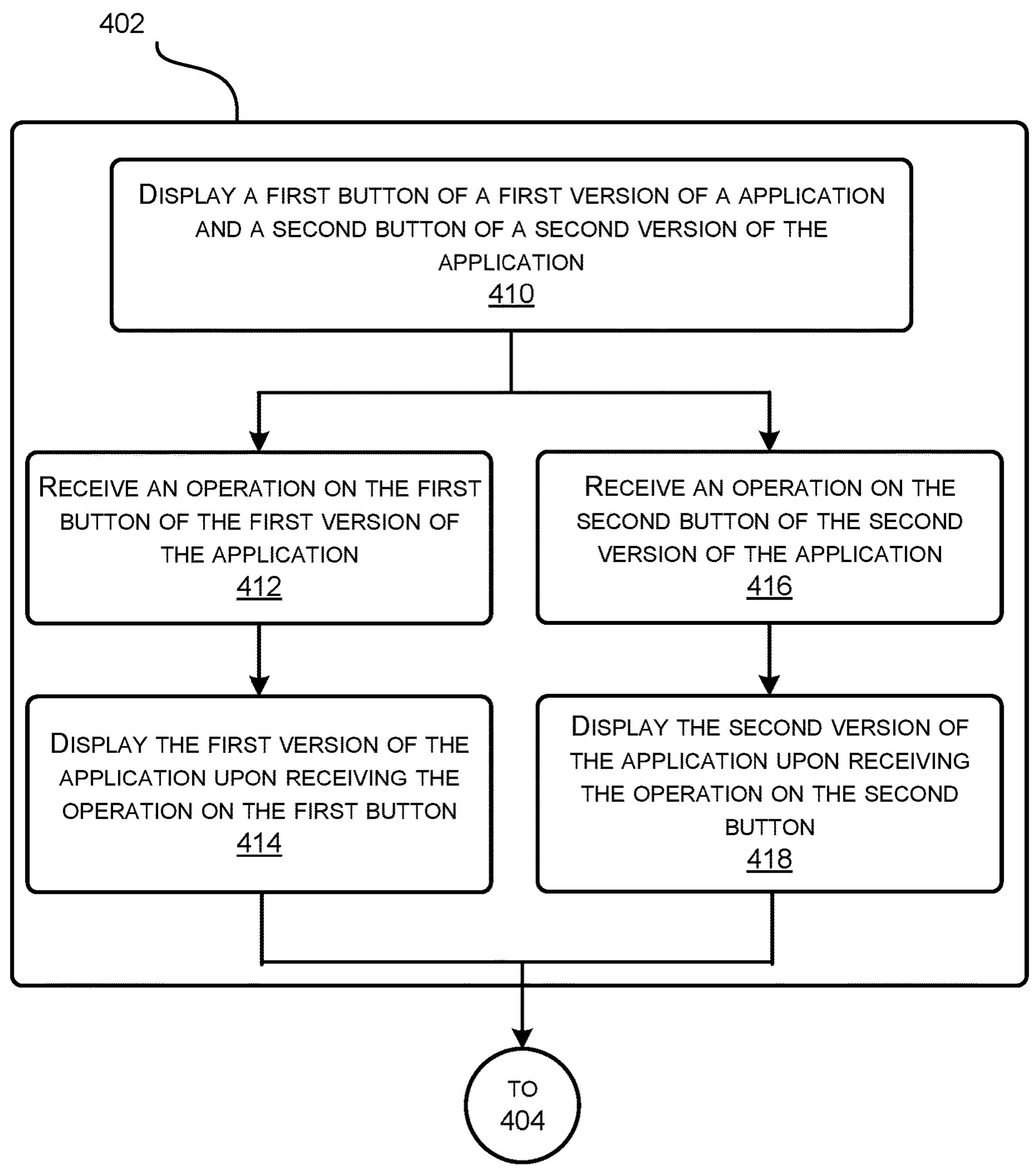

Referring to FIG. 4C, block 402 may include the following.

At block 410, operations may include displaying a first button of a first version of an application and a second button of a second version of the application.

At block 412, operations may include receiving an operation on the first button of the first version of the application.

At block 414, operations may include displaying the first version of the application upon receiving the operation on the first button.

At block 416, operations may include receiving an operation on the second button of the second version of the application.

At block 418, operations may include displaying the second version of the application upon receiving the operation on the second button.

Additional details of the version switching of the application are described throughout the disclosure and are not repeated here.

Figure 4D:
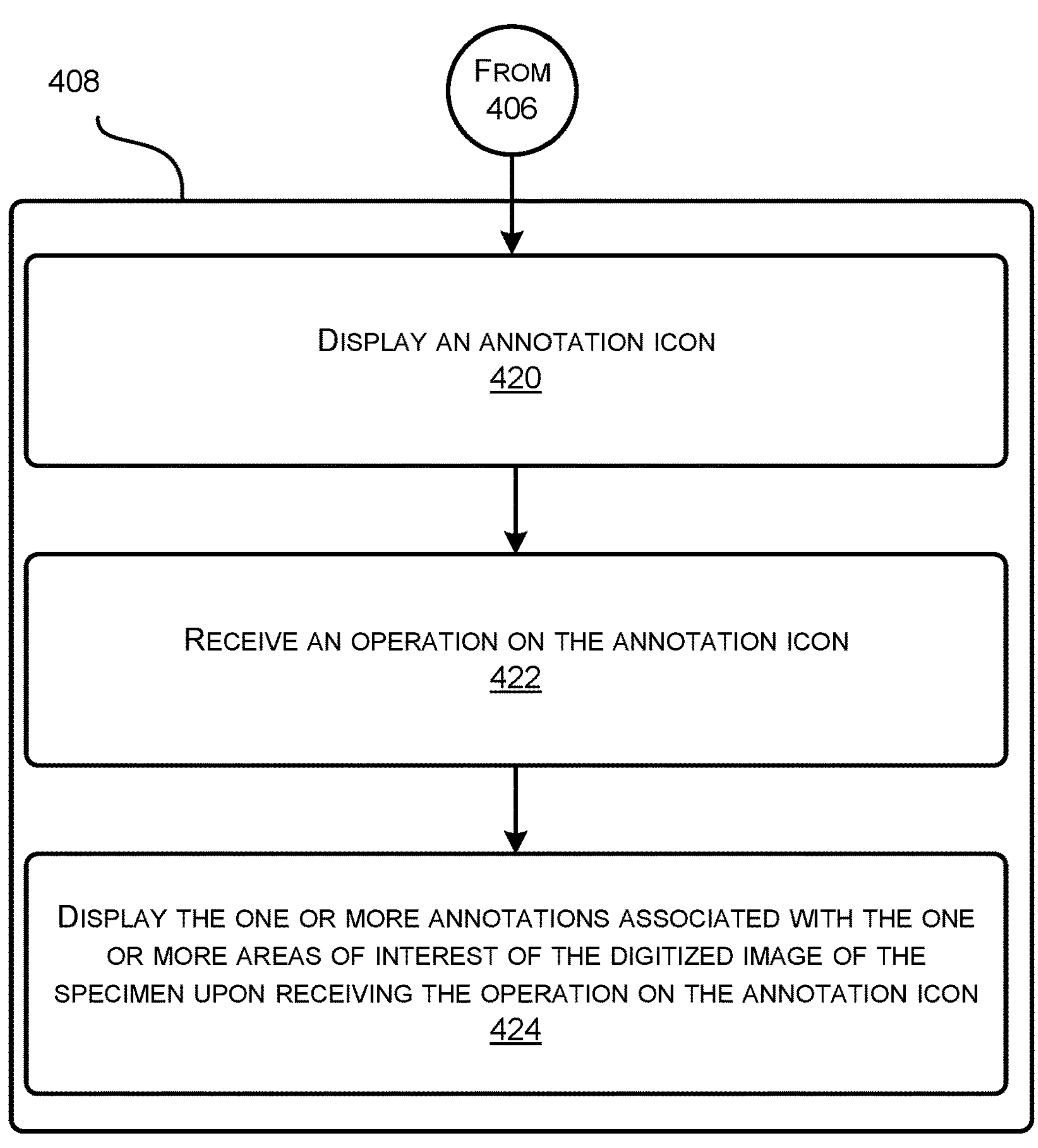

Referring to FIG. 4D, block 408 may include the following.

At block 420, operations may include displaying an annotation icon. The annotation icon may indicate whether one or more annotations associated with one or more areas of interest of the digitized image of the specimen are available for further operations. Additionally, displaying the annotation icon includes displaying an annotation tag, the annotation tag indicating a number of the one or more annotations. Additional details of the annotation icon are described throughout the disclosure and are not repeated here.

At block 422, operations may include receiving an operation on the annotation icon.

At block 424, operations may include displaying the one or more annotations associated with the one or more areas of interest of the digitized image of the specimen upon receiving the operation on the annotation icon.

Figure 4E:
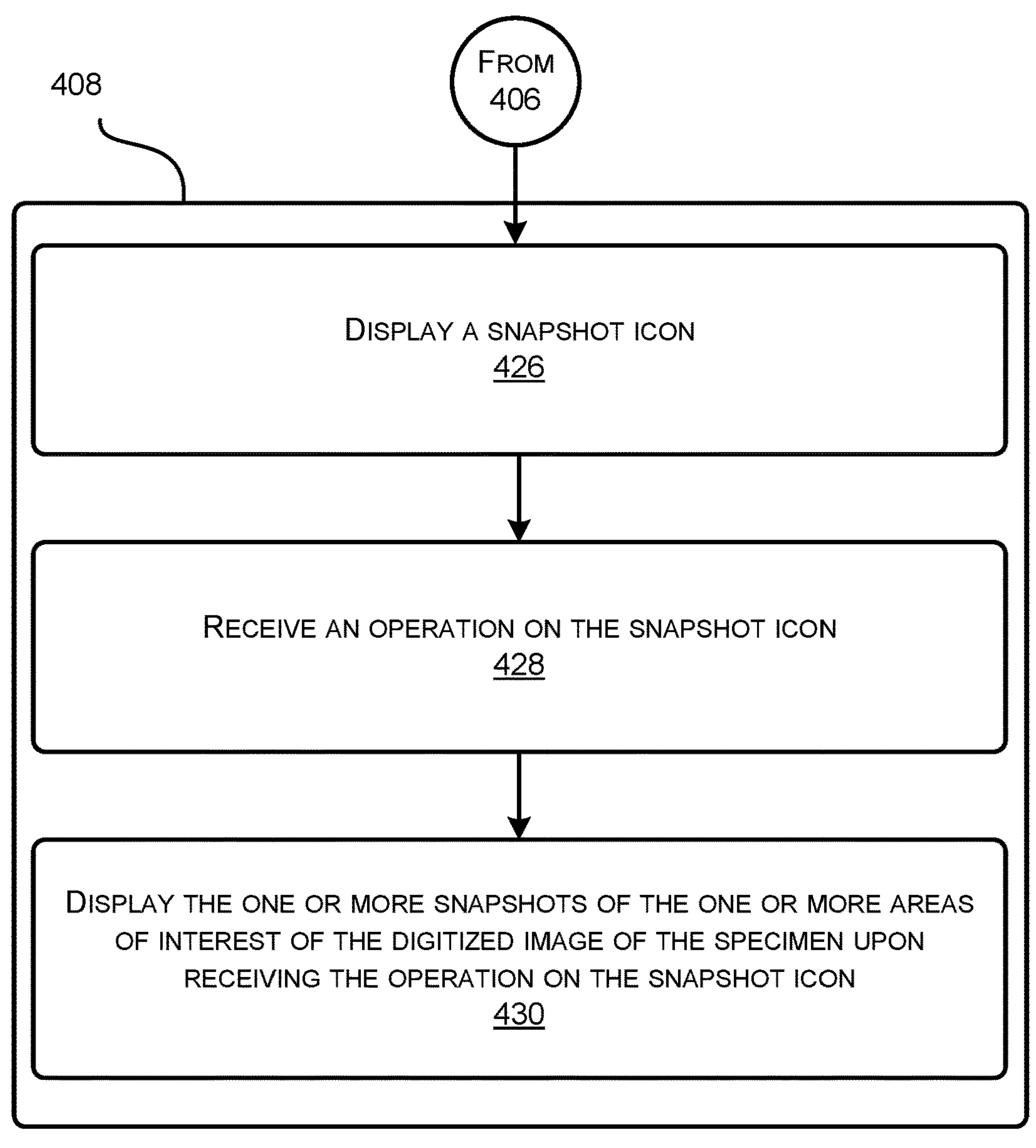

Referring to FIG. 4E, block 408 may include the following.

At block 426, operations may include displaying a snapshot icon. The snapshot icon may indicate whether one or more snapshots associated with one or more areas of interest of the digitized image of the specimen are available for further operations. Additionally, displaying the snapshot icon includes displaying a snapshot tag, the snapshot tag indicating a number of the one or more snapshots. Additional details of the snapshot icon are described throughout the disclosure and are not repeated here.

At block 428, operations may include receiving an operation on the snapshot icon.

At block 430, operations may include displaying the one or more snapshots of the one or more areas of interest of the digitized image of the specimen upon receiving the operation on the snapshot icon.

Figure 4F:
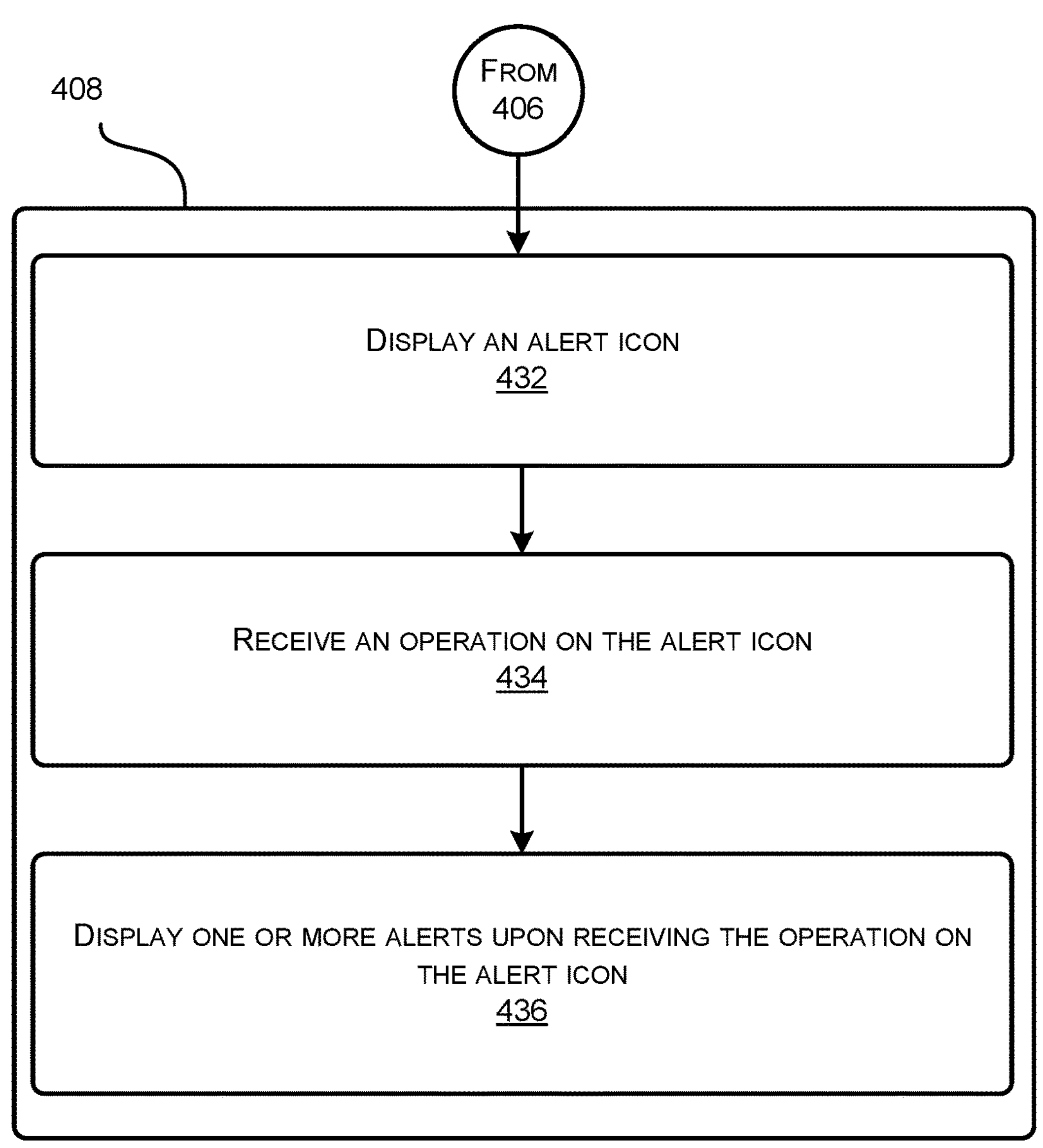

Referring to FIG. 4F, block 408 may include the following.

At block 432, operations may include displaying an alert icon. The alert icon may indicate whether one or more alerts associated with one or more areas of interest of the digitized image of the specimen are available for further operations. Additionally, displaying the alert icon includes displaying an alert tag, the alert tag indicating a number of the one or more alerts. Additional details of the alert icon are described throughout the disclosure and are not repeated here.

At block 434, operations may include receiving an operation on the alert icon.

At block 436, operations may include displaying the one or more alerts upon receiving the operation on the alert icon.

Figure 4G:
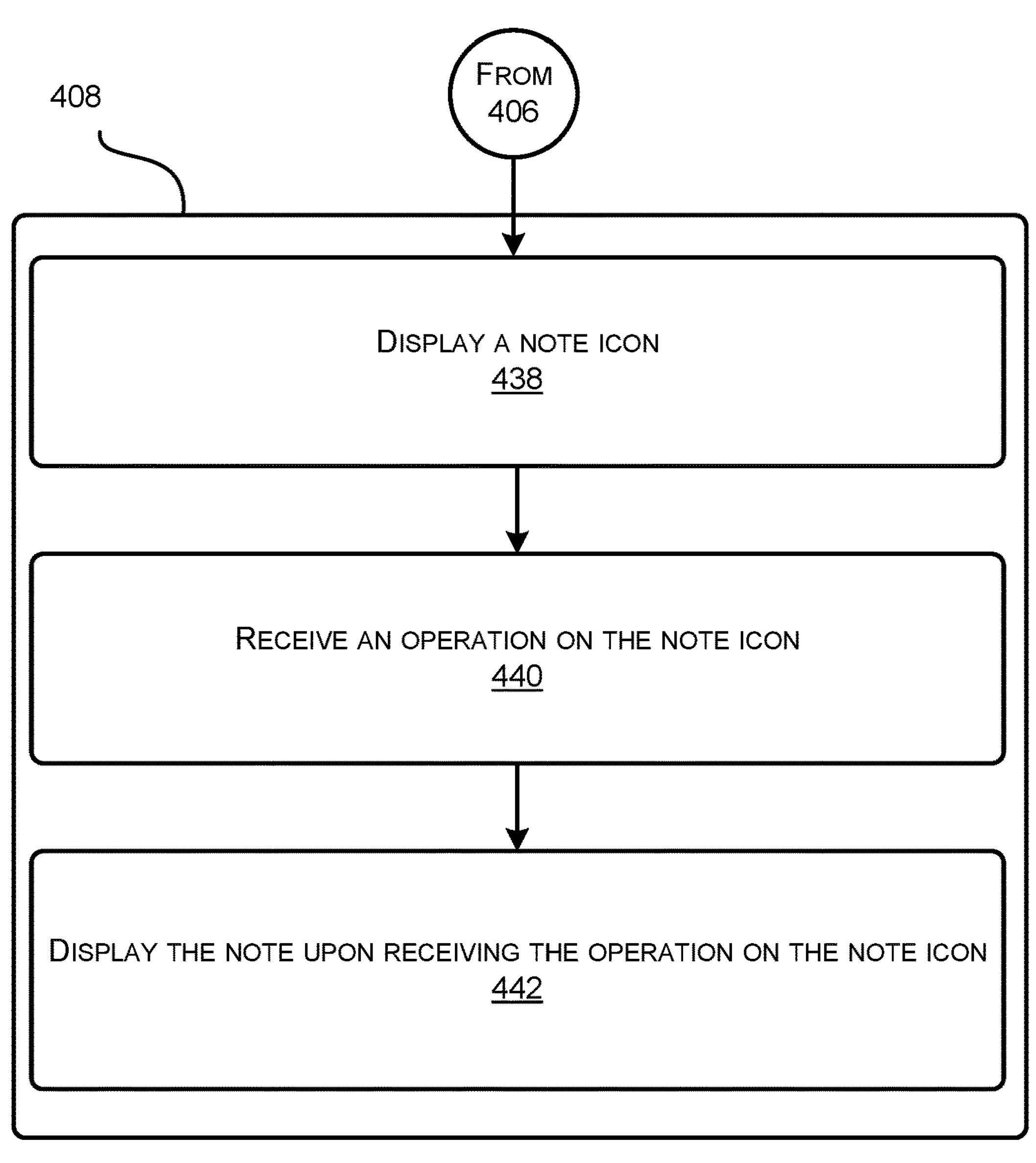

Referring to FIG. 4G, block 408 may include the following.

At block 438, operations may include displaying a note icon. The note icon may indicate whether a note associated with the digitized image of the specimen is available for further operations. Additional details of the note icon are described throughout the disclosure and are not repeated here.

At block 440, operations may include receiving an operation on the note icon.

At block 442, operations may include displaying the note upon receiving the operation on the note icon.

Figure 4H:
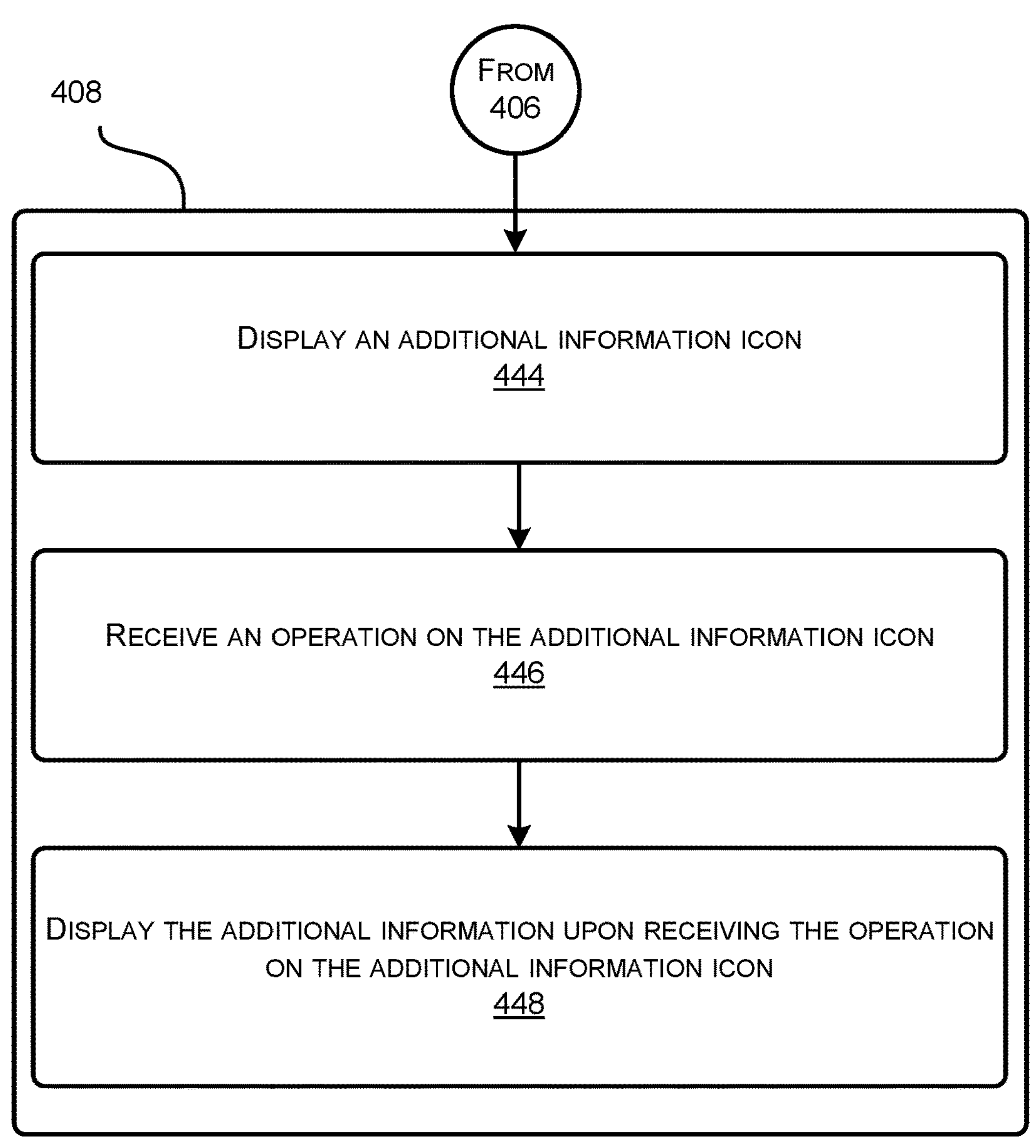

Referring to FIG. 4H, block 408 may include the following.

At block 444, operations may include displaying an additional information icon. The additional information icon may indicate whether additional information associated with the digitized image of the specimen is available for further operations. Additional details of the additional information icon are described throughout the disclosure and are not repeated here.

At block 446, operations may include receiving an operation on the additional information icon.

At block 448, operations may include displaying the additional information upon receiving the operation on the additional information icon.

Figure 4I:
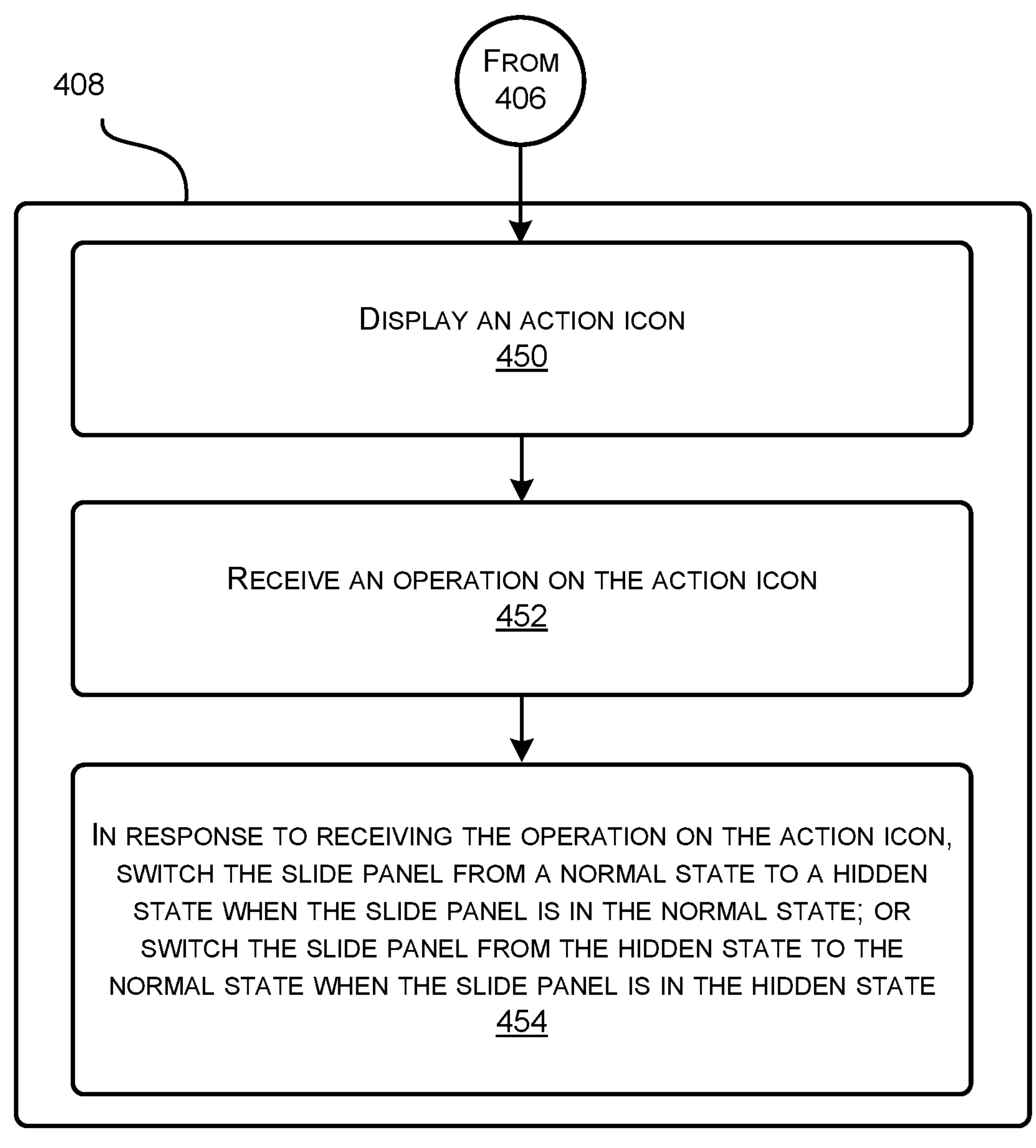

Referring to FIG. 4I, block 408 may include the following.

At block 450, operations may include displaying an action icon. The action icon may indicate whether a follow-up action associated with the digitized image of the specimen is required Additional details of the action icon are described throughout the disclosure and are not repeated here.

At block 452, operations may include receiving an operation on the action icon.

At block 454, operations may include, in response to receiving the operation on the action icon, switching the slide panel from a normal state to a hidden state when the slide panel is in the normal state; or switching the slide panel from the hidden state to the normal state when the slide panel is in the hidden state.

Figure 4J:
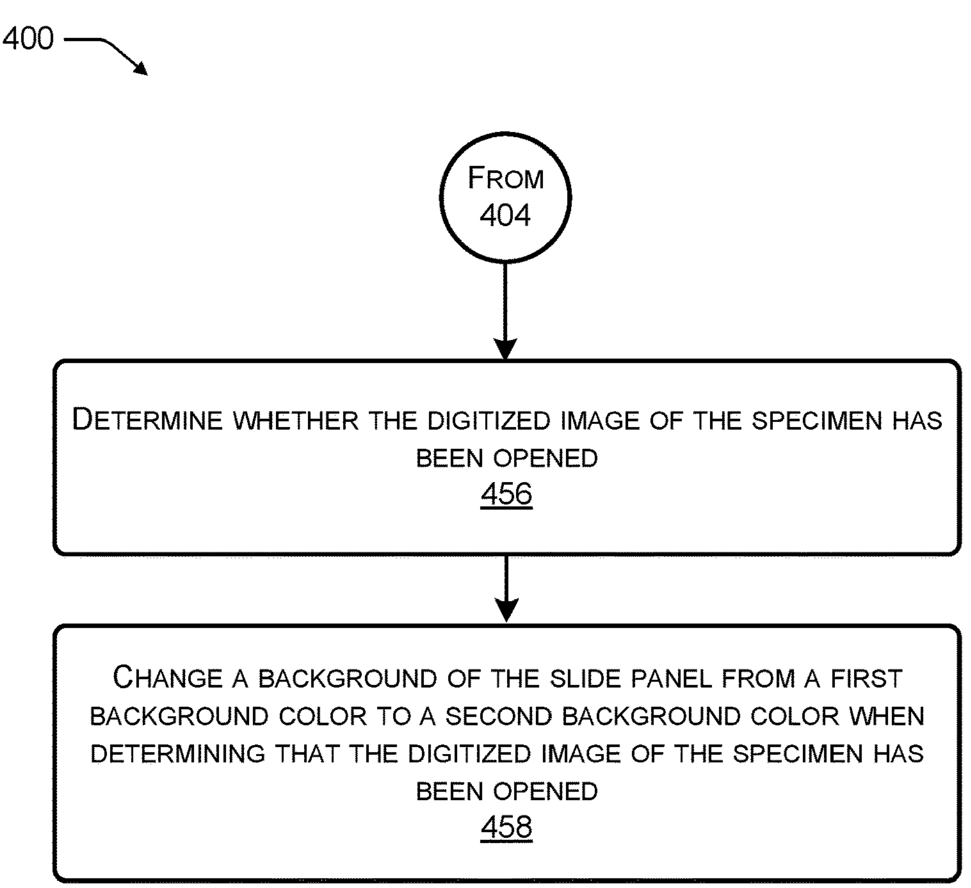

Referring to FIG. 4J, process 400 may include the following.

At block 456, operations may include determining whether the digitized image of the specimen has been opened.

At block 458, operations may include changing a background of the slide panel from a first background color to a second background color when determining that the digitized image of the specimen has been opened.

Figure 4K:
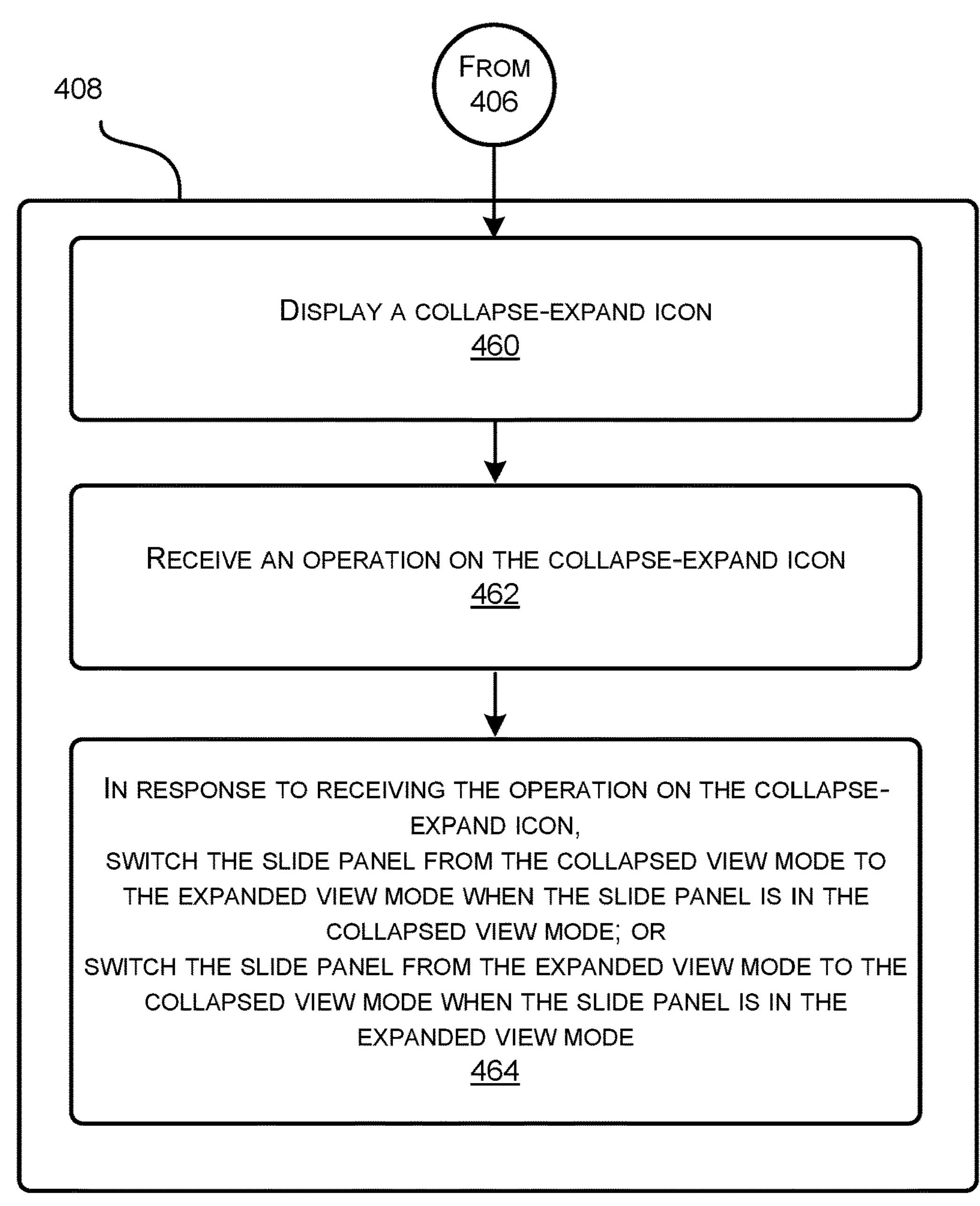

Referring to FIG. 4K, block 408 may include the following.

At block 460, operations may include displaying a collapse-expand icon. The collapse-expand icon may indicate whether the slide panel is in a collapsed view mode or an expanded view mode. Additional details of the collapse-expand icon are described throughout the disclosure and are not repeated here.

At block 462, operations may include receiving an operation on the collapse-expand icon.

At block 464, operations may include, in response to receiving the operation on the collapse-expand icon, switching the slide panel from the collapsed view mode to the expanded view mode when the slide panel is in the collapsed view mode; or switching the slide panel from the expanded view mode to the collapsed view mode when the slide panel is in the expanded view mode.

With the process 400, the one or more interactive icons enable the user to know the status associated with the slide panel without opening the digitized image of the specimen. Additionally, the one or more interactive icons are operable such that the user may view the data associated with the slide panel such as annotations, snapshots, alerts, notes, additional information, follow-up action requirements, and so on by operating the one or more interactive icons without opening the digitized image of the specimen. Additionally, various versions of the same application may be accessible to the user at the same time. Thus, the usability of the digital pathology platform is improved. The workflow of the user may be facilitated.

Figure 5:
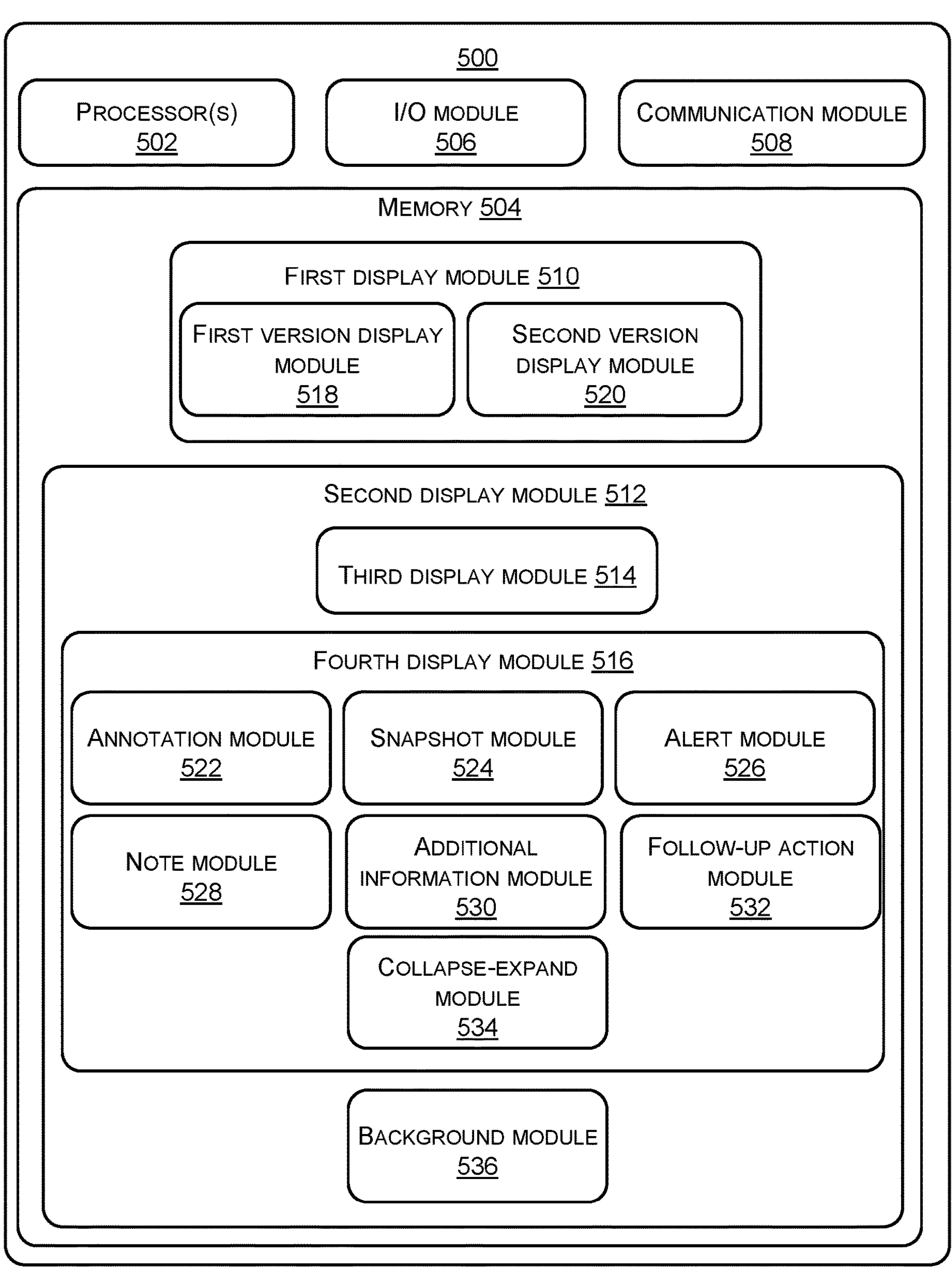
FIG. 5 illustrates an example apparatus for implementing the processes and methods described above.

FIG. 5 illustrates an example apparatus 500 for implementing the processes and methods described above.

The techniques and mechanisms described herein may be implemented by multiple instances of the apparatus 500 as well as by any other computing device, system, and/or environment. The apparatus 500 shown in FIG. 5 is only one example of a system and is not intended to suggest any limitation as to the scope of use or functionality of any computing device utilized to perform the processes and/or procedures described above. Other well-known computing devices, systems, environments and/or configurations that may be suitable for use with the embodiments include, but are not limited to, personal computers, server computers, hand-held or laptop devices, multiprocessor systems, microprocessor-based systems, set top boxes, game consoles, programmable consumer electronics, network PCs, minicomputers, mainframe computers, distributed computing environments that include any of the above systems or devices, implementations using field programmable gate arrays ("FPGAs") and application specific integrated circuits ("ASICs"), and/or the like.

The apparatus 500 may include one or more processors 502 and system memory 504 communicatively coupled to the processor(s) 502. The processor(s) 502 may execute one or more modules and/or processes to cause the processor(s) 502 to perform a variety of functions. In some embodiments, the processor(s) 502 may include a central processing unit (CPU), a graphics processing unit (GPU), both CPU and GPU, or other processing units or components known in the art. Additionally, each of the processor(s) 502 may possess its own local memory, which also may store program modules, program data, and/or one or more operating systems.

Depending on the exact configuration and type of the apparatus 500, the system memory 504 may be volatile, such as RAM, non-volatile, such as ROM, flash memory, miniature hard drive, memory card, and the like, or some combination thereof. The system memory 504 may include one or more computer-executable modules (modules) that are executable by the processor(s) 502.

The apparatus 500 may additionally include an input/output (I/O) interface 506 for receiving data to be processed, and for outputting the processed data. The apparatus 500 may also include a communication module 508 allowing the apparatus 500 to communicate with other devices (not shown) over a network (not shown). The network may include the Internet, wired media such as a wired network or direct-wired connections, and wireless media such as acoustic, radio frequency (RF), infrared, and other wireless media.

The one or more computer-executable modules may include the following.

A first display module 510 may be configured to display a user interface for a digital pathology platform.

A second display module 512 may be configured to display a slide panel on the user interface. Additional details of the slide panel are described throughout the disclosure and are not repeated here.

The second display module 512 may include a third display module 514 and a fourth display module 516.

The third display module 514 may be configured to display a thumbnail of a digitized image of a specimen. Additional details of the thumbnail are described throughout the disclosure and are not repeated here.

The fourth display module 516 may be configured to display one or more interactive icons associated with the slide panel. The one or more interactive icons indicating status associated with the slide panel.

The first display module 510 may include a first version display module 518 and a second version display module 520.

The first version display module 518 may be configured to display a first button of a first version of an application; receive an operation on the first button of the first version of the application; and display the first version of the application upon receiving the operation on the first button.

The second version display module 520 may be configured to display a second button of a second version of the application; receive an operation on the second button of the second version of the application; and display the second version of the application upon receiving the operation on the second button.

Additional details of the version switching of the application are described throughout the disclosure and are not repeated here.

The fourth display module 514 may include an annotation module 522, a snapshot module 524, an alert module 526, a note module 528, an additional information module 530, a follow-up action module 532, and a collapse-expand module 534.

The annotation module 522 may be configured to display an annotation icon. The annotation icon may indicate whether one or more annotations associated with one or more areas of interest of the digitized image of the specimen are available for further operations. Additionally, the annotation module 522 may be further configured to display an annotation tag, the annotation tag indicating a number of the one or more annotations. Additional details of the annotation icon are described throughout the disclosure and are not repeated here.

Additionally, the annotation module 522 may be further configured to receive an operation on the annotation icon; and display the one or more annotations associated with the one or more areas of interest of the digitized image of the specimen upon receiving the operation on the annotation icon.

The snapshot module 524 may be configured to display a snapshot icon. The snapshot icon may indicate whether one or more snapshots associated with one or more areas of interest of the digitized image of the specimen are available for further operations. Additionally, the snapshot module 524 is further configured to display a snapshot tag, the snapshot tag indicating a number of the one or more snapshots. Additional details of the snapshot icon are described throughout the disclosure and are not repeated here.

Additionally, the snapshot module 524 may be further configured to receive an operation on the snapshot icon; and display the one or more snapshots of the one or more areas of interest of the digitized image of the specimen upon receiving the operation on the snapshot icon.

The alert module 526 may be configured to display an alert icon. The alert icon may indicate whether one or more alerts associated with one or more areas of interest of the digitized image of the specimen are available for further operations. Additionally, the alert module 526 is further configured to display an alert tag, the alert tag indicating a number of the one or more alerts. Additional details of the alert icon are described throughout the disclosure and are not repeated here.

Additionally, the alert module 526 is further configured to receive an operation on the alert icon; and display the one or more alerts upon receiving the operation on the alert icon.

The note module 528 may be configured to a note icon. The note icon may indicate whether a note associated with the digitized image of the specimen is available for further operations. Additional details of the note icon are described throughout the disclosure and are not repeated here.

Additionally, the note module 528 may be further configured to receive an operation on the note icon; and display the note upon receiving the operation on the note icon.

The additional information module 530 may be configured to display an additional information icon. The additional information icon may indicate whether additional information associated with the digitized image of the specimen is available for further operations. Additional details of the additional information icon are described throughout the disclosure and are not repeated here.

Additionally, the additional information module 530 may be further configured to receive an operation on the additional information icon; and display the additional information upon receiving the operation on the additional information icon.

The follow-up action module 532 may be configured to display an action icon. The action icon may indicate whether a follow-up action associated with the digitized image of the specimen is required. Additional details of the action icon are described throughout the disclosure and are not repeated here.

Additionally, the follow-up action module 532 may be further configured to receive an operation on the action icon; and in response to receiving the operation on the action icon, switch the slide panel from a normal state to a hidden state when the slide panel is in the normal state, or switch the slide panel from the hidden state to the normal state when the slide panel is in the hidden state.

The collapse-expand module 534 may be configured to display a collapse-expand icon. The collapse-expand icon may indicate whether the slide panel is in a collapsed view mode or an expanded view mode. Additional details of the collapse-expand icon are described throughout the disclosure and are not repeated here.

Additionally, the collapse-expand module 534 may be further configured to receive an operation on the collapse-expand icon; and in response to receiving the operation on the collapse-expand icon, switch the slide panel from the collapsed view mode to the expanded view mode when the slide panel is in the collapsed view mode, or switch the slide panel from the expanded view mode to the collapsed view mode when the slide panel is in the expanded view mode.

The memory 504 may further include a background module 536, which may be configured to determine whether the digitized image of the specimen has been opened; and change a background of the slide panel from a first background color to a second background color when determining that the digitized image of the specimen has been opened.

With the apparatus 500, the one or more interactive icons enable the user to know the status associated with the slide panel without opening the digitized image of the specimen. Additionally, the one or more interactive icons are operable such that the user may view the data associated with the slide panel such as annotations, snapshots, alerts, notes, additional information, follow-up action requirements, and so on by operating the one or more interactive icons without opening the digitized image of the specimen. Additionally, various versions of the same application may be accessible to the user at the same time. Thus, the usability of the digital pathology platform may be improved. The workflow of the user may be facilitated.

Some or all operations of the methods described above may be performed by execution of computer-readable instructions stored on a computer-readable storage medium, as defined below. The term "computer-readable instructions" as used in the description and claims, includes routines, applications, application modules, program modules, programs, components, data structures, algorithms, and the like. Computer-readable instructions may be implemented on various system configurations, including single-processor or multiprocessor systems, minicomputers, mainframe computers, personal computers, hand-held computing devices, microprocessor-based, programmable consumer electronics, combinations thereof, and the like.

The computer-readable storage media may include volatile memory (such as random access memory (RAM)) and/or non-volatile memory (such as read-only memory (ROM), flash memory, etc.). The computer-readable storage media may also include additional removable storage and/or non-removable storage including, but is not limited to, flash memory, magnetic storage, optical storage, and/or tape storage that may provide non-volatile storage of computer-readable instructions, data structures, program modules, and the like.

A non-transient computer-readable storage medium is an example of computer-readable media. Computer-readable media includes at least two types of computer-readable media, namely computer-readable storage media and communications media. Computer-readable storage media includes volatile and non-volatile, removable and non-removable media implemented in any process or technology for storage of information such as computer-readable instructions, data structures, program modules, or other data. Computer-readable storage media includes, but is not limited to, phase-change memory (PRAM), static random-access memory (SRAM), dynamic random-access memory (DRAM), other types of random-access memory (RAM), read-only memory (ROM), electrically erasable programmable read-only memory (EEPROM), flash memory or other memory technology, compact disc read-only memory (CD-ROM), digital versatile discs (DVD) or other optical storage, magnetic cassettes, magnetic tape, magnetic disk storage or other magnetic storage devices, or any other non-transmission medium that may be used to store information for access by a computing device. In contrast, communication media may embody computer-readable instructions, data structures, program modules, or other data in a modulated data signal, such as a carrier wave, or other transmission mechanisms. As defined herein, computer-readable storage media do not include communication media.

The computer-readable instructions stored on one or more non-transitory computer-readable storage media that, when executed by one or more processors, may perform operations described above with reference to the drawings. Generally, computer-readable instructions include routines, programs, objects, components, data structures, and the like that perform particular functions or implement particular abstract data types. The order in which the operations are described is not intended to be construed as a limitation, and any number of the described operations may be omitted or combined in any order and/or in parallel to implement the processes.

CONCLUSION

Although the subject matter has been described in language specific to structural features and/or methodological acts, it is to be understood that the subject matter defined in the appended claims is not necessarily limited to the specific features or acts described. Rather, the specific features and acts are disclosed as illustrative forms of implementing the claims.

EXAMPLE CLAUSES

Clause 1. A method, comprising: displaying a user interface for a digital pathology platform; and displaying a slide panel on the user interface, wherein displaying the slide panel includes displaying a thumbnail of a digitized image of a specimen; and displaying one or more interactive icons associated with the slide panel, the one or more interactive icons indicating status associated with the slide panel.

Clause 2. The method of clause 1, wherein displaying the user interface for the digital pathology platform includes displaying a first button of a first version of an application and a second button of a second version of the application.

Clause 3. The method of clause 2, further comprising: receiving an operation on the first button of the first version of the application; and displaying the first version of the application upon receiving the operation on the first button.

Clause 4. The method of clause 2, further comprising: receiving an operation on the second button of the second version of the application; and displaying the second version of the application upon receiving the operation on the second button.

Clause 5. The method of clause 1, wherein displaying the one or more interactive icons associated with the slide panel includes displaying an annotation icon, the annotation icon indicating whether one or more annotations associated with one or more areas of interest of the digitized image of the specimen are available for further operations.

Clause 6. The method of clause 5, wherein displaying the annotation icon includes displaying an annotation tag, the annotation tag indicating a number of the one or more annotations.

Clause 7. The method of clause 5, further comprising: receiving an operation on the annotation icon; and displaying the one or more annotations associated with the one or more areas of interest of the digitized image of the specimen upon receiving the operation on the annotation icon.

Clause 8. The method of clause 1, wherein displaying the one or more interactive icons associated with slide panel includes displaying a snapshot icon, the snapshot icon indicating whether one or more snapshots of one or more areas of interest of the digitized image of the specimen are available for further operations.

Clause 9. The method of clause 8, wherein displaying the snapshot icon includes displaying a snapshot tag, the snapshot tag indicating a number of the one or more snapshots.

Clause 10. The method of clause 8, further comprising: receiving an operation on the snapshot icon; and displaying the one or more snapshots of the one or more areas of interest of the digitized image of the specimen upon receiving the operation on the snapshot icon.

Clause 11. The method of clause 1, wherein displaying the one or more interactive icons associated with slide panel includes displaying an alert icon, the alert icon indicating whether one or more alerts associated with the digitized image of the specimen are available for further operations.

Clause 12. The method of clause 11, wherein displaying the alert icon includes displaying an alert tag, the alert tag indicating a number of the one or more alerts.

Clause 13. The method of clause 11, further comprising: receiving an operation on the alert icon; and displaying the one or more alerts upon receiving the operation on the alert icon.

Clause 14. The method of clause 1, wherein displaying the one or more interactive icons associated with the slide panel includes displaying a note icon, the note icon indicating whether a note associated with the digitized image of the specimen is available for further operations.

Clause 15. The method of clause 14, further comprising: receiving an operation on the note icon; and displaying the note upon receiving the operation on the note icon.

Clause 16. The method of clause 1, wherein displaying the one or more interactive icons associated with the slide panel includes displaying an additional information icon, the additional information icon indicating whether additional information associated with the digitized image of the specimen is available for further operations.

Clause 17. The method of clause 16, further comprising: receiving an operation on the additional information icon; and displaying the additional information upon receiving the operation on the additional information icon.

Clause 18. The method of clause 1, wherein displaying the one or more interactive icons associated with slide panel includes displaying an action icon, the action icon indicating whether a follow-up action associated with the digitized image of the specimen is required.

Clause 19. The method of clause 18, further comprising: receiving an operation on the action icon; and in response to receiving the operation on the action icon, switching the slide panel from a normal state to a hidden state when the slide panel is in the normal state; or switching the slide panel from the hidden state to the normal state when the slide panel is in the hidden state.

Clause 20. The method of clause 1, further comprising: determining whether the digitized image of the specimen has been opened; and changing a background of the slide panel from a first background color to a second background color when determining that the digitized image of the specimen has been opened.

Clause 21. The method of clause 1, wherein displaying the one or more interactive icons associated with the slide panel includes displaying a collapse-expand icon, the collapse-expand icon indicating whether the slide panel is in a collapsed view mode or an expanded view mode.

Clause 22. The method of clause 21, further comprising: receiving an operation on the collapse-expand icon; and in response to receiving the operation on the collapse-expand icon, switching the slide panel from the collapsed view mode to the expanded view mode when the slide panel is in the collapsed view mode; or switching the slide panel from the expanded view mode to the collapsed view mode when the slide panel is in the expanded view mode.

Clause 23. An apparatus, comprising: one or more processors; memory, coupled to the one or more processors, the memory storing thereon computer-executable modules, executable by the one or more processors, the computer-executable modules including a first display module configured to display a user interface for a digital pathology platform; a second display module configured to display a slide panel on the user interface, wherein the second display module includes a third display module configured to display a thumbnail of a digitized image of a specimen on the user interface; and a fourth display module configured to display one or more interactive icons associated with the slide panel, the one or more interactive icons indicating status associated with the slide panel.

Clause 24. One or more computer-readable media, stored thereon computer-readable instructions that, when executed by one or more processors, cause the one or more processors to perform acts comprising: displaying a user interface for a digital pathology platform; and displaying a slide panel on the user interface, wherein displaying the slide panel includes displaying a thumbnail of a digitized image of a specimen; and displaying one or more interactive icons associated with the slide panel, the one or more interactive icons indicating status associated with the slide panel.

Clause 25. The one or more computer-readable media of clause 24, wherein displaying the user interface for the digital pathology platform includes displaying a first button of a first version of an application and a second button of a second version of the application.

What is claimed is:

1. A method comprising:

displaying a user interface for a digital pathology platform, wherein the displaying the user interface for the digital pathology platform includes displaying, at the user interface, a first button associated with a first software version of an application and a second button associated with a second software version of the application, wherein the second software version of the application includes slide panel actions that are not available in the first software version of the application, and slide panel actions of the first software version and the slide panel actions of the second software version are accessible simultaneously; and displaying a slide panel on the user interface, wherein the displaying the slide panel includes:

displaying a thumbnail of a digitized image of a specimen;

displaying, along a side of the thumbnail of the digitized image of the specimen, one or more interactive icons associated with the slide panel and indicating a status associated with the slide panel, the one or more interactive icons including an annotation icon indicative of whether one or more annotations associated with one or more areas of interest of the digitized image of the specimen are available for further operations;

displaying, as part of the one or more interactive icons associated with the slide panel, an additional information icon configured to cause display of an image magnification of the digitized image of the specimen, wherein displaying the additional information icon includes at least one of changing a color, size, or shape of the additional information icon;

displaying, as part of the one or more interactive icons associated with the slide panel, a collapse-expand icon indicative of whether the slide panel is in a collapsed view mode or an expanded view mode;

receiving a first operation on the annotation icon, and displaying the one or more annotations in response to receiving the first operation on the annotation icon;

receiving a second operation on the additional information icon, and displaying the image magnification in response to receiving the second operation on the additional information icon; and receiving a third operation on the collapse-expand icon, and displaying the slide panel in the expanded view mode in response to receiving the third operation on the collapse-expand icon, wherein displaying the expanded view mode comprises displaying, proximate to the thumbnail of the digitized image, a source of the specimen, a stain type of the specimen, and a body part of the specimen.

2. The method of claim 1, further comprising:

receiving an operation on the first button of the first software version of the application; and displaying the first software version of the application upon receiving the operation on the first button.

3. The method of claim 1, wherein the displaying the annotation icon includes displaying an annotation tag, the annotation tag indicating a number of the one or more annotations.

4. The method of claim 3, wherein the number of the one or more annotations is associated with a first annotation associated with the one or more areas of interest and by a first pathologist, and a second annotation associated with the one or more areas of interest and by a second pathologist.

5. The method of claim 1, wherein the displaying the one or more interactive icons associated with the slide panel includes displaying a snapshot icon, the snapshot icon indicating whether one or more snapshots of one or more areas of interest of the digitized image of the specimen are available for further operations.

6. The method of claim 5, further comprising:

receiving an operation on the snapshot icon; and displaying the one or more snapshots of the one or more areas of interest of the digitized image of the specimen upon receiving the operation on the snapshot icon.

7. The method of claim 1, wherein the displaying the one or more interactive icons associated with the slide panel includes displaying an alert icon, the alert icon indicating whether one or more alerts associated with the digitized image of the specimen are available for further operations.

8. The method of claim 7, further comprising:

receiving an operation on the alert icon; and displaying the one or more alerts upon receiving the operation on the alert icon.

9. The method of claim 1, wherein the displaying the one or more interactive icons associated with the slide panel includes displaying a note icon, the note icon indicating whether a note associated with the digitized image of the specimen is available for further operations.

10. The method of claim 9, further comprising:

receiving an operation on the note icon; and displaying the note upon receiving the operation on the note icon.

11. The method of claim 1, wherein the displaying the one or more interactive icons associated with the slide panel includes displaying an action icon, the action icon indicating whether a follow-up action associated with the digitized image of the specimen is required.

12. The method of claim 11, further comprising:

receiving an operation on the action icon; and in response to receiving the operation on the action icon:

switching the slide panel from a normal state to a hidden state when the slide panel is in the normal state; or switching the slide panel from the hidden state to the normal state when the slide panel is in the hidden state.

13. The method of claim 1, further comprising:

determining whether the digitized image of the specimen has been opened; and changing a background of the slide panel from a first background color to a second background color when it is determined that the digitized image of the specimen has been opened.

14. The method of claim 1, further comprising:

receiving an operation on the collapse-expand icon; and in response to receiving the operation on the collapse-expand icon:

switching the slide panel from the collapsed view mode to the expanded view mode when the slide panel is in the collapsed view mode; or switching the slide panel from the expanded view mode to the collapsed view mode when the slide panel is in the expanded view mode.

15. The method of claim 1, wherein the additional information icon is further configured to cause display of at least one of:

an image size of the digitized image;

an image resolution of the digitized image; or a scanner type of the digitized image, the scanner type indicating a scanner used to generate the digitized image.

16. The method of claim 1, wherein displaying the one or more interactive icons associated with the slide panel and including the annotation icon further comprises:

displaying a highlighted version of the annotation icon and indicating that the one or more annotations associated with the one or more areas of interest are available for the further operations; or displaying an unhighlighted version of the annotation icon and indicating that the one or more annotations associated with the one or more areas of interest are unavailable for the further operations.

17. The method of claim 1, wherein the slide panel actions of the second software version at least partially include changing an order of slide panels displayed on the user interface.

18. An apparatus comprising:

one or more processors;

memory, coupled to the one or more processors, the memory storing thereon computer-executable modules, executable by the one or more processors, the computer-executable modules including:

a first display module configured to display a user interface for a digital pathology platform, wherein displaying the user interface for the digital pathology platform includes displaying, at the user interface, a first button associated with a first software version of an application and a second button associated with a second software version of the application, wherein the second software version of the application includes slide panel actions that are not available in the first software version of the application, and slide panel actions of the first software version and the slide panel actions of the second software version are accessible simultaneously; and a second display module configured to display a slide panel on the user interface, wherein the second display module includes:

a third display module configured to display a thumbnail of a digitized image of a specimen on the user interface; and a fourth display module configured to:

display, along a side of the thumbnail of the digitized image of the specimen, one or more interactive icons associated with the slide panel and indicating status associated with the slide panel, the one or more interactive icons including an annotation icon indicative of whether one or more annotations associated with one or more areas of interest of the digitized image of the specimen are available for further operations;

display, as part of the one or more interactive icons associated with the slide panel, an additional information icon configured to cause display of an image magnification of the digitized image of the specimen, wherein the display of the additional information icon includes at least one of a change of color, size, or shape of the additional information icon;

display, as part of the one or more interactive icons associated with the slide panel, a collapse-expand icon indicative of whether the slide panel is in a collapsed view mode or an expanded view mode;

receive a first operation on the annotation icon, and display the one or more annotations in response to receiving the first operation on the annotation icon;

receive a second operation on the additional information icon, and display the image magnification in response to receiving the second operation on the additional information icon; and receive a third operation on the collapse-expand icon, and display the slide panel in the expanded view mode in response to receiving the third operation on the collapse-expand icon, wherein displaying the expanded view mode comprises displaying, proximate to the thumbnail of the digitized image, a source of the specimen, a stain type of the specimen, and a body part of the specimen.

19. A system comprising:

one or more non-transitory computer-readable media, stored thereon computer-readable instructions that, when executed by one or more processors, cause the one or more processors to perform acts comprising:

displaying a user interface for a digital pathology platform wherein the displaying the user interface for the digital pathology platform includes displaying, at the user interface, a first button associated with a first software version of an application and a second button associated with a second software version of the application, wherein the second software version of the application includes slide panel actions that are not available in the first software version of the application, and slide panel actions of the first software version and the slide panel actions the second software version are accessible simultaneously; and displaying a slide panel on the user interface, wherein the displaying the slide panel includes:

displaying a thumbnail of a digitized image of a specimen;

displaying, along a side of the thumbnail of the digitized image of the specimen, one or more interactive icons associated with the slide panel and indicating status associated with the slide panel, the one or more interactive icons including an annotation icon indicating whether one or more annotations associated with one or more areas of interest of the digitized image of the specimen are available for further operations;

displaying, as part of the one or more interactive icons associated with the slide panel, an additional information icon configured to cause display of an image magnification of the digitized image of the specimen, wherein displaying the additional information icon includes at least one of changing a color, size, or shape of the additional information icon;

displaying, as part of the one or more interactive icons associated with the slide panel, a collapse-expand icon indicative of whether the slide panel is in a collapsed view mode or an expanded view mode;

receiving a first operation on the annotation icon, and displaying the one or more annotations in response to receiving the first operation on the annotation icon;

receiving a second operation on the additional information icon, and displaying the image magnification in response to receiving the second operation on the additional information icon; and receiving a third operation on the collapse-expand icon, and displaying the slide panel in the expanded view mode in response to receiving the third operation on the collapse-expand icon, wherein displaying the expanded view mode comprises displaying, proximate to the thumbnail of the digitized image, a source of the specimen, a stain type of the specimen, and a body part of the specimen.

20. The system of claim 19, the acts further comprising:

receiving an operation on the first button of the first software version of the application; and displaying the first software version of the application upon receiving the operation on the first button.

* * * * *